United States Patent [19]

Ura et al.

[11] Patent Number: 4,629,493
[45] Date of Patent: Dec. 16, 1986

[54] HETEROCYCLIC ETHER TYPE PHENOXY FATTY ACID DERIVATIVES AND HERBICIDAL COMPOSITION

[75] Inventors: Yasukazu Ura; Gozyo Sakata; Kenzi Makino; Yasuo Kawamura, all of Funabashi; Yuzi Kawamura, Shiraoka; Takasi Ikai, Shiraoka; Tosihiko Oguti, Shiraoka, all of Japan

[73] Assignee: Nissan Chemical Industries Ltd., Tokyo, Japan

[21] Appl. No.: 116,381

[22] Filed: Jan. 29, 1980

[30] Foreign Application Priority Data

Feb. 22, 1979 [JP] Japan .................. 54-20164

[51] Int. Cl.[4] .................. C07D 241/44; C07D 215/22; A01N 43/60; A01N 43/42
[52] U.S. Cl. .................. 71/92; 544/354; 546/157; 71/94
[58] Field of Search .................. 544/354; 71/92

[56] References Cited

U.S. PATENT DOCUMENTS

| | | | |
|---|---|---|---|
| 3,040,046 | 6/1962 | Sasse | 544/354 |
| 3,260,726 | 7/1966 | Sasse | 544/354 |
| 3,415,878 | 12/1968 | Sasse | 544/354 |
| 3,472,848 | 10/1969 | Cragoe | 544/344 |
| 3,582,315 | 6/1971 | Sopor | 544/356 |
| 3,752,812 | 8/1973 | Abushanab | 544/354 |
| 3,928,608 | 12/1975 | Cox | 544/354 |
| 4,046,553 | 9/1977 | Takahashi | 546/302 |
| 4,115,102 | 9/1978 | Takahashi | 71/94 |
| 4,391,628 | 7/1983 | Rempfler | 544/354 |

OTHER PUBLICATIONS

Nordmann, Chem Abs 78, 29817t (1972).
Handte et al, Chem Abs 88, 190816h (1978).

*Primary Examiner*—Mark L. Berch
*Attorney, Agent, or Firm*—Oblon, Fisher, Spivak, McClelland, & Maier

[57] ABSTRACT

A herbicidal composition which comprises an adjuvant and an active ingredient of heterocyclic ether type phenoxy fatty acid derivative having the formula

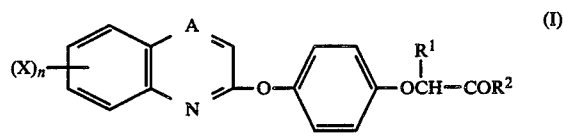

wherein A represents —CH— or —N—; X represents a halogen atom; n is 0, 1 or 2; $R^1$ represents a hydrogen atom; a lower alkyl group; $R^2$ represents —OH; —O-alkyl group; —OM group (M is an inorganic or organic salt moiety);

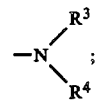

—O-lower alkenyl group; —O-benzyl group; —O-lower alkylalkoxy group; —O-phenyl; —O-cyclohexyl, —O-halogenoalkyl, —O-lower alkynyl and —O-cyanoalkyl; $R^3$ and $R^4$ respectively represent a hydrogen atom or a lower alkyl group.

17 Claims, No Drawings

HETEROCYCLIC ETHER TYPE PHENOXY FATTY ACID DERIVATIVES AND HERBICIDAL COMPOSITION

BACKGROUND OF THE INVENTION

1. Field of the Invention

The present invention relates to novel heterocyclic ether type phenoxy fatty acid derivatives (hereinafter referring to the compound of the present invention) and herbicidal compositions containing the same.

2. Description of the Prior Arts

Various compounds have been practically used as herbicides as a result of various studies on herbicides for long years. These herbicides have been proposed and practically used to contribute for elimination of agricultural labour works and to improve productivities of agricultural and horticultural crop plants.

It has been still awaited to find novel herbicides having superior herbicidal characteristics. The herbicides for agricultural and horticultural purposes are preferably compounds which selectively control the object weeds at a small dose without a toxicity to the crop plants. The known herbicides do not always have the optimum herbicidal characteristics.

The inventors have studied to develop novel useful herbicides especially on herbicidal characteristics of various heterocyclic compounds.

Substituted pyridyloxyphenoxy fatty acid herbicides have been known as heterocyclic ether type phenoxy fatty acid derivatives in Japanese Unexamined Patent Publication No. 106735/1976.

Benzimidazole, benzthiazole, and benzoxazole derivatives and herbicidal effect of these compounds have been known in Japanese Unexamined Patent Publication No. 40767/1978.

SUMMARY OF THE INVENTION

It is an object of the present invention to provide novel heterocyclic ether type phenoxy fatty acid derivatives.

It is another objects of the present invention to provide a herbicidal composition which has excellent herbicidal activity to various weeds especially gramineous weeds but substantially nonphytotoxicity to broad leaf crop plants.

The other object of the present invention is to provide a process for producing such herbicidal compound.

The foregoing and other objects of the present invention have been attained by providing novel compounds having the formula

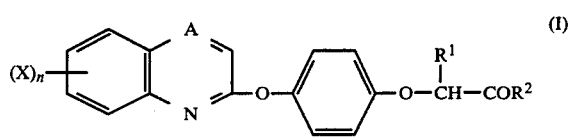

wherein A represents —CH— or —N—; X represents a halogen atom; n is 0, 1 or 2; $R^1$ represents a hydrogen atom or a lower alkyl group; $R^2$ represents —OH; —O—alkyl group; —OM group (M is an inorganic or organic salt moiety);

O—lower alkenyl group; O—benzyl group; O—lower alkylalkoxy group; O—phenyl; —O—cyclohexyl; —O—halogenoalkyl, —O—lower alkynyl and —O—cyanoalkyl; $R^3$ and $R^4$ respectively represent a hydrogen atom or a lower alkyl group.

In the formula (I), $R^2$ can be —OM group which can be —ONa, —OK, —O—½Ca, —O—½Mg, —OH lower alkylamine group, —OH ethanolamine group, —OH lower alkyl ethanolamine group or —ONH$_4$ group. Such compounds are water soluble and can be used as an aqueous solution.

DETAILED DESCRIPTION OF THE PREFERRED EMBODIMENTS

The heterocyclic ether type phenoxy fatty acid derivatives having quinoline or quinoxaline ring and having the formula (I) of the present invention are the novel compounds.

The heterocyclic ether type phenoxy fatty acid derivatives (I) of the present invention are significantly unique compounds which are effective for controlling gramineous weeds without any phytotoxicity to broad leaf crop plants as well as broad leaf weeds especially in a post-emergence treatment. Such unique characteristics have not been found.

Typical compounds of the present invention having the formula (I) are shown in Table (1) together with the physical properties. The present invention are not limited to the typical compounds shown in Table 1.

TABLE 1

| Comp. No. | A | X | $R^1$ | $R^2$ | Physical property |
|---|---|---|---|---|---|
| 1 | CH | H | CH$_3$ | OH | mp 188–189° C. W.C. |
| 2 | CH | H | CH$_3$ | OCH$_3$ | mp 98–99° C. W.C. |
| 3 | CH | H | CH$_3$ | OC$_2$H$_5$ | oily at room temp. |
| 4 | CH | 6-Cl | CH$_3$ | OC$_2$H$_5$ | $n_D^{19.7}$ = 1.5814 |
| 5 | CH | H | CH$_3$ | ONa | mp > 280° C. W.C. |
| 6 | CH | H | CH$_3$ | N(CH$_3$)$_2$ | mp 108–109° C. W.C. |
| 7 | CH | H | H | OCH$_3$ | oily at room temp. |
| 8 | N | H | CH$_3$ | OH | mp > 280° C. W.C. |
| 9 | N | H | CH$_3$ | OCH$_3$ | mp 130–132° C. W.C. |
| 10 | N | H | CH$_3$ | OC$_2$H$_5$ | mp 75–76° C. W.C. |

TABLE 1-continued $$\text{(X)}_n\text{-benzene-quinoxaline(A,N)-O-} \underset{R^1}{\underset{|}{CH}}-COR^2 \text{ via phenylene-O}$$

| No. | A | (X)n | R¹ | OR² | Properties |
|---|---|---|---|---|---|
| 11 | N | 6-Cl, 7-Cl | CH₃ | OCH₃ | mp 113–115° C. W.C. |
| 12 | N | H | CH₃ | N(CH₃)₂ | mp 152–153° C. W.C. |
| 13 | CH | 6-F | CH₃ | OH | mp 158–159° C. W.C. |
| 14 | CH | 6-F | CH₃ | OCH₃ | mp 97° C. W.C. |
| 15 | CH | 6-F | CH₃ | OC₂H₅ | mp 60–61° C. W.C. |
| 16 | CH | 6-Br | CH₃ | OH | mp 171–172° C. W.C. |
| 17 | CH | 6-Br | CH₃ | OCH₃ | mp 117° C. W.C. |
| 18 | CH | 6-Br | CH₃ | OC₂H₅ | mp 96–97° C. W.C. |
| 19 | CH | 6-I | CH₃ | OCH₃ | mp 126–127° C. W.C. |
| 20 | CH | 6-I | CH₃ | OC₂H₅ | colorless liq. $n_D^{20} = 1.6237$ |
| 21 | N | 6-Cl | CH₃ | OH | mp 130–132.5° C. W.C. |
| 22 | N | 6-Cl | CH₃ | OCH₃ | mp 124–125° C. W.C. |
| 23 | N | 6-Cl | CH₃ | OC₂H₅ | mp 84–85° C. W.C. |
| 24 | N | 6-Cl | CH₃ | OC₃H₇—i | mp 98–100° C. W.C. |
| 25 | N | 6-F | CH₃ | OH | mp 200–201° C. W.C. |
| 26 | N | 6-F | CH₃ | OCH₃ | mp 124–125° C. W.C. |
| 27 | N | 6-F | CH₃ | OC₂H₅ | mp 78–79° C. W.C. |
| 28 | N | 6-F | CH₃ | OC₃H₇—i | mp 111–112.5° C. W.C. |
| 29 | CH | 6-Cl | CH₃ | OH | mp 176–177° C. W.C. |
| 30 | CH | 6-Cl | CH₃ | OCH₃ | mp 94–95° C. W.C. |
| 31 | CH | 6-Cl | CH₃ | N(CH₃)₂ | mp 122–123° C. W.C. |
| 32 | CH | 6-F | CH₃ | OC₃H₇—n | pale yellow liq. $n_D^{19} = 1.5700$ |
| 33 | CH | 6-F | CH₃ | OC₃H₇—i | colorless liq. $n_D^{20} = 1.5632$ |
| 34 | CH | 6-F | CH₃ | OC₄H₉—n | mp 45.5–47° C. W.C. |
| 35 | CH | 6-F | CH₃ | OC₄H₉—i | colorless liq. $n_D^{20} = 1.5593$ |
| 36 | CH | 6-F | CH₃ | OC₄H₉—t | pale yellow liq. $n_D^{20} = 1.5580$ |
| 37 | CH | 6-F | CH₃ | OC₅H₁₁—n | colorless liq. $n_D^{20.5} = 1.5572$ |
| 38 | CH | 6-F | CH₃ | OCH₂—C₆H₅ | pale yellow $n_D^{20} = 1.5972$ |
| 39 | CH | 6-F | CH₃ | O(CH₂)₂OCH₃ | mp 62–63° C. W.C. |
| 40 | CH | 6-F | CH₃ | OCH₂CH=CH₂ | colorless liq. $n_D^{21} = 1.5728$ |
| 41 | N | 6-Br | CH₃ | OH | mp 165–167° C. W.C. |
| 42 | N | 6-Br | CH₃ | OCH₃ | mp 127–128.5° C. W.C. |
| 43 | N | 6-Br | CH₃ | OC₂H₅ | mp 72–73° C. W.C. |
| 44 | N | 6-Br | CH₃ | OC₃H₇—i | mp 118–120° C. W.C. |
| 45 | N | 6-I | CH₃ | OCH₃ | mp 122–124° C. W.C. |
| 46 | N | 6-Br | CH₃ | ONa | mp > 250° C. W.C. |
| 47 | N | 6-Cl | CH₃ | OC₃H₇—n | mp 75.5–77° C. W.C. |
| 48 | N | 6-Cl | CH₃ | OC₄H₉—n | mp 76.5–77.5° C. W.C. |
| 49 | N | 6-Cl | CH₃ | OC₄H₉—i | pale yellow liq. $n_D^{20.5} = 1.5728$ |
| 50 | N | 6-Cl | CH₃ | OC₄H₉—sec | mp 73.5–74.5° C. W.C. |
| 51 | N | 6-Cl | CH₃ | OC₄H₉—t | pale yellow liq. $n_D^{20.5} = 1.5608$ |
| 52 | N | 6-Cl | CH₃ | OC₅H₁₁—n | mp 78–79.5° C. W.C. |
| 53 | N | 6-Cl | CH₃ | O—cyclohexyl | mp 88.5–90° C. W.C. |
| 54 | N | 6-Cl | CH₃ | O—C₆H₅ | mp 110–112° C. W.C. |
| 55 | N | 6-Cl | CH₃ | OCH₂—C₆H₅ | mp 93–94° C. W.C. |

TABLE 1-continued

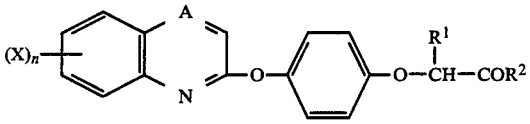

| | | | | | |
|---|---|---|---|---|---|
| 56 | N | 6-Cl | CH₃ | O(CH₂)₂OCH₃ | mp 74–76.5° C. W.C. |
| 57 | N | 6-Cl | CH₃ | OCH₂CH=CH₂ | mp 55–56.5° C. W.C. |
| 58 | N | 6-Cl | CH₃ | N(CH₃)₂ | mp 136.5–137.5° C. W.C. |
| 59 | N | 6-F | CH₃ | ONa | mp >250° C. W.C. |
| 60 | N | 6-F | CH₃ | OC₃H₇—n | mp 68–69° C. W.C. |
| 61 | N | 6-F | CH₃ | OC₄H₉—n | mp 74–75° C. W.C. |
| 62 | N | 6-F | CH₃ | OC₄H₉—i | mp 81–82° C. W.C. |
| 63 | N | 6-F | CH₃ | OC₅H₁₁—n | mp 70–71° C. W.C. |
| 64 | N | 6-F | CH₃ | OCH₂CH=CH₂ | mp 76–77.5° C. W.C. |
| 65 | N | 6-F | CH₃ | O(CH₂)₂OCH₃ | mp 92–93.5° C. W.C. |
| 66 | N | 6-F | CH₃ | O—CH₂—C₆H₅ | mp 111–114° C. W.C. |
| 67 | N | 6-Cl, 7-Cl | CH₃ | OH | mp 167.0–169° C. W.C. |
| 68 | N | 6-Cl, 7-Cl | CH₃ | OC₂H₅ | mp 127.5–129° C. W.C. |
| 69 | N | 6-Cl, 7-Cl | CH₃ | OC₃H₇—i | mp 168–169.5° C. W.C. |
| 70 | N | 6-Cl, 7-Cl | CH₃ | O(CH₂)₂OCH₃ | mp 113–114° C. W.C. |
| 71 | N | 6-Cl, 7-Cl | CH₃ | N(CH₃)₂ | mp 140–141° C. W.C. |
| 72 | N | 6-Cl | CH₃ | O—N(CH₃)₃ / CH₂CH₂OH | mp 91–95° C. W.C. |
| 73 | N | 6-F | CH₃ | OH₂N(CH₂CH₂OH)₂ | $n_D^{20}$ 1.5840 liq. |
| 74 | N | 6-F | CH₃ | OH₃N(CH₂)₂CH₃ | mp 158–165° C. W.C. |
| 75 | N | 6-Cl | CH₃ | ONH₄ | mp 112–118° C. W.C. |
| 76 | N | 6-Cl | CH₃ | OH₃NCH₃ | mp 85–92° C. W.C. |
| 77 | N | 6-Cl | CH₃ | OH₂N(CH₃)₂ | mp 63–67° C. W.C. |

| | Compound | Optical rotation $[\alpha]_D^{temp.}$ (solvent concentration) | Physical property |
|---|---|---|---|
| 78 | 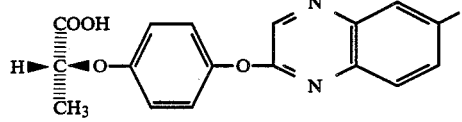 | $[\alpha]_D^{27} = +22.9°$ (CH₃OH; C = 0.33%) | mp. 151–153° C. W.C. |
| 79 | 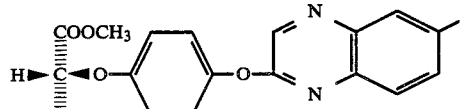 | $[\alpha]_D^{31} = +30.0°$ (CHCl₃; C = 1.16%) | mp. 142–144° C. W.C. |
| 80 | 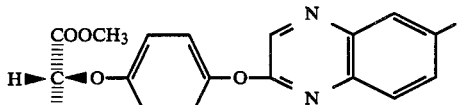 | $[\alpha]_D^{31} = +32.8°$ (CHCl₃; C = 1.20%) | mp. 112–114° C. W.C. |
| 81 | 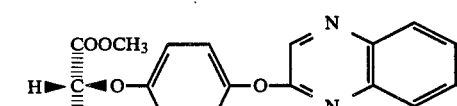 | $[\alpha]_D^{31} = +32.4°$ (CHCl₃; C = 1.15%) | mp. 144–146° C. W.C. |
| 82 | 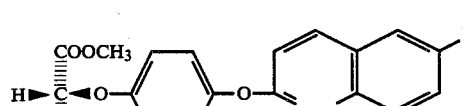 | $[\alpha]_D^{32} = +31.2°$ (CHCl₃; C = 1.18%) | mp. 90–91° C. W.C. |

TABLE 1-continued

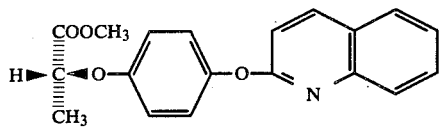

| Comp. No. | A | X | R[1] | R[2] | Physical property |
|---|---|---|---|---|---|
| 83 | (structure shown: COOCH₃, H►C◄O—phenyl—O—quinoline, CH₃) | | | | $[\alpha]_D^{32} = +36.4°$ (CHCl₃; C = 0.99%) mp. 91-92° C. W.C. |
| 84 | N | 6-Cl | CH₃ | O(CH₂)₂Cl | mp 69.5-71° C. W.C. |
| 85 | N | 6-F | CH₃ | OCH₂C≡CH | $n_D^{21}$ 1.5781 liq. |
| 86 | N | 6-F | CH₃ | OCH₂CN | mp 110-111° C. W.C. |
| 87 | N | 6-Cl | CH₃ | OCH₂CN | mp 116-118° C. W.C. |

NMR SPECTRUM OF COMPOUNDS

| Compound No. | |
|---|---|
| 1 | (δ ppm, DMSO-d₆); 1.55(3H,d), 4.7(1H,q), 6.7-8.2 (10H,m), 11.0(1H) |
| 2 | (δ ppm, CDCl₃); 1.6(3H,d), 3.7(3H,s), 4.7(1H,q), 6.7-8.0(10H,m) |
| 3 | (δ ppm, CDCl₃); 1.2(3H,t), 1.6(3H,d), 4.15(2H,q), 4.65(1H,q), 6.75-8.05(10H,m) |
| 4 | (δ ppm, CDCl₃); 1.2(3H,t), 1.6(3H,d), 4.15(2H,q), 4.65(1H,q), 6.8-8.0(9H,m) |
| 5 | — |
| 6 | (δ ppm, CDCl₃); 1.6(3H,d), 3.0(6H,d), 4.9(1H,q), 6.8-8.1(10H,m) |
| 7 | (δ ppm, CDCl₃); 3.75(3H,s), 4.55(2H,s), 6.7-8.1(10H,m) |
| 8 | — |
| 9 | (δ ppm, CDCl₃); 1.6(3H,d), 3.75(3H,s), 4.75(1H,q), 6.9(2H,d), 7.2(2H,d), 7.4-8.2(4H,m), 8.6(1H,s) |
| 10 | (δ ppm, CDCl₃); 1.28(3H,t), 1.6(3H,d), 4.20(2H,q), 4.75(1H,q), 6.8-7.80(8H,m), 8.60(1H,s) |
| 11 | (δ ppm, CDCl₃); 1.6(3H,d), 3.71(3H,s), 4.70(1H,q), 6.8-8.1(6H,m), 8.50(1H,s) |
| 12 | (δ ppm, CDCl₃); 1.55(3H,d), 3.0(6H,d), 4.9(1H,q), 6.8-7.8(8H,m), 8.55(1H,s) |
| 13 | (δ ppm, DMSO-d₆); 1.55(3H,d), 4.8(1H,q), 6.8-8.4(9H,m), 12.9(1H,b s) |
| 14 | (δ ppm, CDCl₃); 1.6(3H,d), 3.7(3H,s), 4.7(1H,q), 6.75-8.0(9H,m) |
| 15 | (δ ppm, CDCl₃); 1.25(3H,t), 1.6(3H,d), 4.2(2H,q), 4.7(1H,q), 6.7-8.0(9H,m) |
| 16 | (δ ppm, DMSO-d₆); 1.55(3H,d), 4.8(1H,q), 6.8-8.4 (9H,m), 13.0(1H,b s) |
| 17 | (δ ppm), CDCl₃; 1.6(3H,d), 3.7(3H,s), 4.7(1H,q), 6.7-8.0(9H,m) |
| 18 | (δ ppm, CDCl₃); 1.2(3H,t), 1.6(3H,d), 4.15(2H,q), 4.7(1H,q), 6.7-8.0(9H,m) |
| 19 | (δ ppm, CDCl₃); 1.6(3H,d), 3.7(3H,s), 4.7(1H,q), 6.7-8.0(9H,m) |
| 20 | (δ ppm, CDCl₃); 1.2(3H,t), 1.6(3H,d), 4.2(2H,q), 4.7(1H,q), 6.7-8.0(9H,m) |
| 21 | (δ ppm, DMSO-d₅); 1.55(3H,d), 4.86(1H,q), 6.98 (2H,d), 7.30(2H,d), 7.77(2H,b s), 8.12(1H,b s), 8.87(1H,s) |
| 22 | (δ ppm, CDCl₃); 1.63(3H,d), 3.79(3H,s), 4.78 (1H,q), 6.93(2H,d), 7.21(2H,d), 7.64(2H,b s), 8.07(1H,b s), 8.67(1H,s) |
| 23 | (δ ppm, CDCl₃); 1.26(3H,t), 1.63(3H,d), 4.24(2H,q), 4.76(1H,q), 6.93(2H,d), 7.20(2H,d), 7.64(2H,b s), 8.06(1H,b s), 8.66(1H,s) |
| 24 | (δ ppm, CDCl₃); 1.24(3H,d), 1.33(3H,d), 1.67(3H,d), 4.76(1H,q), 5.14(1H,m), 6.96(2H,d), 7.23(2H,d), 7.65(2H,b s), 8.08(1H,b s), 8.70(1H,s) |
| 25 | (δ ppm, DMSO-d₆); 1.60(3H,d), 4.72(1H,q), 6.94 (2H,d), 7.21(2H,d), 7.37-7.96(3H,m), 8.70(1H,s) |
| 26 | (δ ppm, CDCl₃); 1.65(3H,d), 3.77(3H,s), 4.80(1H,q), 6.92(2H,d), 7.21(2H,d), 7.40-7.88(3H,m), 8.66(1H,s) |
| 27 | (δ ppm, CDCl₃); 1.26(3H,t), 1.63(3H,d), 4.24(2H,q), 4.76(1H,q), 6.92(2H,d), 7.19(2H,d), 7.36-7.95(3H,m), 8.63(1H,s) |
| 28 | (δ ppm, CDCl₃); 1.20(3H,d), 1.27(3H,d), 1.62(3H, d), 4.70(1H,q), 5.07(1H,m), 6.89(2H,d), 7.16(2H,d) 7.3-7.85(3H,m), 8.61(1H,s) |
| 29 | (δ ppm, DMSO-d₆); 1.56(3H,d), 4.84(1H,q); [6.80-8.40, 9H—6.91(2H,d), 7.17(2H,d), 7.75(2H,s), 7.96(1H,s), 8.27(1H,d)] |
| 30 | (δ ppm, CDCl₃); 1.57(3H,d), 3.68(3H,s), 4.68(1H,q); [6.75-8.10, 9H—6.83(2H,d), 7.13(2H,d), 7.96(1H,d)] |
| 31 | (δ ppm, CDCl₃); 1.59(3H,d), 2.92(3H,s), 3.08(3H, s), 4.91(1H,q); [6.75-8.05, 9H—6.84(2H,d), 7.13 (2H,d), 7.91(1H,d)] |
| 32 | (δ ppm, CDCl₃); 0.85(3H,t), 1.60(3H,d), 1.71(2H, m), 4.11(2H,t), 4.72(1H,q); [6.75-8.15, 9H—6.88 (2H,d), 7.14(2H,d), 7.94(1H,d)] |
| 33 | (δ ppm, CDCl₃); 1.19(3H,d), 1.26(3H,d), 1.59(3H, d), 4.65(1H,q), 5.04(1H,m); [6.75-8.10, 9H—6.84 (2H,d), 7.13(2H,d), 7.92(1H,d)] |
| 34 | (δ ppm, CDCl₃); 0.88(3H,t), 1.00-2.10(4H,m), 1.60 (3H,d), 4.15(2H,t), 4.73(1H,q); [6.70-8.15, 9H—6.90(2H,d), 7.15(2H,d), 7.95(1H,d)] |
| 35 | (δ ppm, CDCl₃); 0.88(6H,d), 1.62(3H,d), Ca. 1.85 (1H,m), 3.92(2H,d), 4.73(1H,q); [6.75-8.10, 9H—6.86(2H,d), 7.11(2H,d), 7.95(1H,d)] |
| 36 | (δ ppm, CDCl₃); 1.43(9H,s), 1.58(3H,d), 4.63(1H, q); [6.80-8.10, 9H—6.91(2H,d), 7.18(2H,d), 7.94 (1H,d)] |
| 37 | (δ ppm, CDCl₃); 0.87(3H,t), 1.05-1.55(6H,m), 1.62 (3H,d), 4.17(2H,t), 4.74(1H,q); [6.80-8.15, 9H—6.91(2H,d), 7.19(2H,d), 7.99(1H,d)] |
| 38 | (δ ppm, CDCl₃); 1.62(3H,d), 4.78(1H,q), 5.20(2H,s); [6.75-8.15, 14H—6.88(2H,d), 7.15(2H,d), 7.97(1H,d)] |
| 39 | (δ ppm, CDCl₃); 1.63(3H,d), 3.33(3H,s), 3.60(2H,t), 4.32(2H,t), 4.77(1H,q); [6.75-8.20, 9H—6.90(2H,d), 7.15(2H,d), 8.00(1H,d)] |
| 40 | (δ ppm, CDCl₃); 1.63(3H,d), 4.67(2H,d), 4.78(1H,q), (5.00-6.20, 3H,m); [6.80-8.10, 9H—6.91(2H,d), 7.08 (2H,d), 7.90(1H,d)] |
| 41 | (δ ppm, DMSO-d₆), 1.53(3H,d), 4.79(1H,q); [6.75-8.85, 8H—6.93(2H,d), 7.22(2H,d), 7.69(2H,b s), 8.19(1H,s), 8.75(1H,s)] |
| 42 | (δ ppm, CDCl₃); 1.63(3H,d), 3.74(3H,s), 4.74(1H,q), [6.75-8.70, 8H—6.90(2H,d), 7.19(2H,d), 7.61(2H, b s, 8.17(1H,b s), 8.61(1H,s)] |
| 43 | (δ ppm, CDCl₃); 1.25(3H,t), 1.63(3H,d), 4.24(2H, q); 4.76(1H,q); [6.80-8.70, 8H—6.96(2H,d), 7.24(2H, d), 7.66(2H,b s), 8.19(1H,b s), 8.65(1H,s)] |
| 44 | (δ ppm, CDCl₃); 1.20(3H,d), 1.27(3H,d), 1.61(3H, d), 4.71(1H,q), 5.08(1H,m) [6.80-8.70, 8H—6.92 (2H,d), 7.18(2H,d), 7.60(2H,b s), 8.17(1H,b s), 8.60(1H,s)] |
| 45 | (δ ppm, CDCl₃); 1.63(3H,d), 3.76(3H,s), 4.77(1H,q); |

NMR SPECTRUM OF COMPOUNDS

| Compound No. | |
|---|---|
| 46 | — |
| 47 | (δ ppm, CDCl₃); 0.90(3H,t), 1.64(3H,d), 1.66(2H,m), 4.13(2H,t), 4.76(1H,q); [6.80-8.70, 8H—6.92(2H,d), 7.21(2H,d), 7.59(2H,b s), 8.00(1H,b s), 8.62(1H,s)] |
| 48 | (δ ppm, CDCl₃); 0.91(3H,t), 1.64(3H,d), 1.00-1.90 4H,m), 4.18(2H,t), 4.76(1H,q); [6.80-8.70, 8H—6.92 (2H,d), 7.21(2H,d), 7.62(2H,b s), 8.03(1H,b s), 8.65(1H,s)] |
| 49 | (δ ppm, CDCl₃); 0.88(6H,d), 1.64(3H,d), Ca. 1.95 (1H,m), 3.96(2H,d), 4.77(1H,q); [6.80-8.70, 8H—6.91(2H,d), 7.18(2H,d), 7.56(2H,b s), 7.98(1H,b s) 8.60(1H,s)] |
| 50 | (δ ppm, CDCl₃); 0.92(3H,t), 1.21(3H,t), 1.63(3H,d), 1.30-1.90(2H,m), 4.74(1H,q), Ca. 4.92(1H,m); [6.80-8.75, 8H—6.95(2H,d), 7.20(2H,d), 7.60(2H,b s), 8.02(1H,b s), 8.63(1H,s)] |
| 51 | (δ ppm, CDCl₃); 1.44(9H,s), 1.60(3H,d), 4.64(1H,q); [6.80-8.70, 8H—6.91(2H,d), 7.19(2H,d), 7.57(2H,b s) 7.99(1H,b s), 8.61(1H,s)] |
| 52 | (δ ppm, CDCl₃); 0.88(3H,t), 1.65(3H,d), 1.10-1.90 (6H,m), 4.18(2H,t), 4.77(1H,q); [6.80-8.75, 8H—6.95(2H,d), 7.22(2H,d), 7.63(2H,b s), 8.04(1H,b s) 8.66(1H,s)] |
| 53 | (δ ppm, CDCl₃); 1.00-2.10(10H,m), 1.62(3H,d), 4.71 (1H,q), Ca. 4.81(1H,m); [6.80-8.70, 8H—6.92(2H,d), 7.17(2H,d), 7.58(2H,b s), 8.00(1H,b s)] |
| 54 | (δ ppm, CDCl₃); 1.78(3H,d), 4.95(1H,q); [6.80-8.75, 13H—7.57(2H,b s), 7.99(1H,b s), 8.61(1H,s)] |
| 55 | (δ ppm, CDCl₃); 1.64(3H,d), 4.77(1H,q), 5.19(2H, s); [6.75-8.70, 13H—6.86(2H,d), 7.14(2H,d), 7.28 (5H,b s), 7.59(2H,b s), 8.01(1H,b s), 8.62(1H,s)] |
| 56 | (δ ppm, CDCl₃); 1.63(3H,d), 3.30(3H,s), 3.54(2H,t), 4.32(2H,t), 4.76(1H,q); [6.80-8.70, 8H—6.90(2H,d), 7.15(2H,d), 7.53(2H,b s), 7.94(1H,b s), 8.57(1H,s)] |
| 57 | (δ ppm, CDCl₃); 1.65(3H,d), 4.68(2H,d), 4.80(1H,q), (5.05-6.30, 3H); [6.80-8.75, 8H—6.95(2H,d), 7.22 (2H,d), 7.63(2H,b s), 8.04(1H,b s), 8.65(1H,s)] |
| 58 | (δ ppm, CDCl₃); 1.60(3H,d), 2.94(3H,s), 3.10(3H,s), 4.94(1H,q); [6.80-8.70, 8H—6.87(2H,d), 7.14(2H,d), 7.53(2H,b s), 7.93(1H,b s), 8.55(1H,s)] |
| 59 | (δ ppm, D₂O); 1.61(3H,d), 4.71(1H,q); [6.80-8.80, 8H—6.93(2H,d), 7.21(2H—d), 7.37-7.96(3H,m) 8.70 (1H,s)] |
| 60 | (δ ppm, CDCl₃); 0.89(3H,t), 1.64(3H,d), 1.65(2H, m), 4.13(2H,t), 4.76(1H,q); [6.80-8.80, 8H—6.93 (2H,d), 7.18(2H,d), 8.74(1H,s)] |
| 61 | (δ ppm, CDCl₃); 0.90(3H,t), 1.10-1.85(4H,m), 1.62 (3H,d), 4.16(2H,t), 4.73(1H,q); [6.80-8.70, 8H—6.92(2H,d), 7.18(2H,d), 8.64(1H,s)] |
| 62 | (δ ppm, CDCl₃); 0.89(6H,d), 1.65(3H,d), Ca. 2.02 (1H,m), 3.97(2H,d), 4.78(1H,q); [6.80-8.80, 8H—6.92 (2H,d), 7.20(2H,d), 8.61(1H,s)] |
| 63 | (δ ppm, CDCl₃); 0.89(3H,t), 1.10-1.95(6H,m), 1.66 (3H,d), 4.17(2H,t), 4.76(1H,q); [6.80-8.80, 8H—6.91(2H,d), 7.19(2H,d), 8.63(1H,s)] |
| 64 | (δ ppm, CDCl₃); 1.66(3H,d), 4.67(2H,d), 4.79 (1H,q); [5.05-6.40, 3H,m]; [6.80-8.75, 8H—6.93 (2 H,d), 7.19(2H,d), 8,65(1H,s)] |
| 65 | (δ ppm, CDCl₃); 1.64(3H,d), 3.32(3H,s), 3.55(2H, t), 4.33(2H,t), 4.79(1H,q); [6.80-8.75, 8H—6.92 (2H,d), 7.17(2H,d), 8.65(1H,s)] |
| 66 | (δ ppm, CDCl₃); 1.62(3H,d), 4.76(1H,q), 5.19(2H,s); [6.80-8.65, 13H—6.88(2H,d), 7.16(2H,d), 8.65(1H,s)] |
| 67 | (δ ppm, DMSO-d₆); 1.53(3H,d) 4.82(1H,q), 6.95(2H, d), 7.26(2H,d), 8.00(1H,s), 8.30(1H,s), 8.87(1H,s) |
| 68 | (δ ppm, CDCl₃); 1.27(3H,t), 1.64(3H,d), 4.25(2H,q), 4.75(1H,q), 6.92(2H,d), 7.16(2H,d), 7.83(1H,s), 8.12(1H,s), 8.62(1H,s) |
| 69 | (δ ppm, CDCl₃); 1.20(3H,d), 1.26(3H,d), 1.62(3H, d), 4.71(1H,q), 5.09(1H,m), 6.90(2H,d), 7.17(2H, d), 7.82(1H,s), 8.11(1H,s), 8.61(1H,s) |
| 70 | (δ ppm, CDCl₃), 1.63(3H,d), 3.31(3H,s), 3.55(2H,t), 4.31(2H,t), 4.77(1H,q), 6.91(2H,d), 7.15(2H,d), 7.82(1H,s), 8.10(1H,s), 8.60(1H,s) |
| 71 | (δ ppm, CDCl₃); 1.63(3H,d), 2.99(3H,s), 3.15(3H,s), 3.99(1H,q), 6.92(2H,d), 7.17(2H,d), 7.81(1H,s), 8.09(1H,s), 8.60(1H,s) |
| 78 | (δ ppm, DMSO-d₆); 1.54(3H,d), 4.86(1H,q); [6.80-8.90, 8H—6.94(2H,d), 7.25(2H,d), 7.45-8.05 (3H,m), 8.85(1H,s)] |
| 79 | (δ ppm, CDCl₃); 1.62(3H,d), 3.75(2H,s), 4.75(1H,q); [6.80-8.70, 8H—6.89(2H,d), 7.17(2H,d), 7.30-7.90 (3H,m), 8.65(1H,s)] |
| 80 | (δ ppm, CDCl₃); 1.61.(3H,d), 3.76(3H,s), 4.75 (1H,q); [6.80-8.70, 8H—6.92(2H,d), 7.19(2H,d), 7.63(2H,b s), 8.04(1H,b s), 8.65(1H,s)] |
| 81 | (δ ppm, CDCl₃); 1.61(3H,d), 3.75(3H,s), 4.74(1H,q); [6.80-8.70, 9H—6.91(2H,d), 7.19(2H,d), 7.45-8.25 (4H,m), 8.62(1H,s)] |
| 82 | (δ ppm, CDCl₃); 1.63(3H,d), 3.76(3H,s), 4.75(1H,q); [6.80-8.20, 9H—6.91(2H,d), 7.17(2H,d), 7.17(2H,d), 8.02(1H,d)] |
| 83 | (δ ppm, CDCl₃); 1.61(3H,d), 3.75(3H,s), 4.76(1H, q); [6.80-8.20, 10H—6.92(2H,d), 7.18(2H,d), 8.07 (1H,d)] |
| 84 | (δ ppm, CDCl₃); 1.67(3H,d), 3.68(2H,t), 4.43(2H,t) 4.81(1H,q), 6.95(2H,d), 7.20(2H,d), 7.61(2H,b s), 8.03(1H,b s), 8.67(1H,s) |
| 85 | (δ ppm, CDCl₃); 1.66(3H,d), 2.52(1H,t), 4.56-4.98 (3H,m), 6.95(2H,d), 7.26(2H,d), 7.32-7.85(3H,m), 8.65(1H,s) |
| 86 | (δ ppm, CDCl₃); 4.78(2H,s), 4.85(1H,q), 1.69(3H,d), 6.89(2H,d), 7.20(2H,d), 7.32-7.85(3H,m) |
| 87 | (δ ppm, CDCl₃); 1.68(3H,d), 4.77(2H,s), 4.83(1H,q), 6.87(2H,d), 7.18(2H,d), 7.57(2H,b s), 7.97(1H,b s), 8.60(1H,s) |

The compound (I) of the present invention can be produced by the following processes.

(A) The compound of the present invention can be produced by a condensation of a compound having the formula

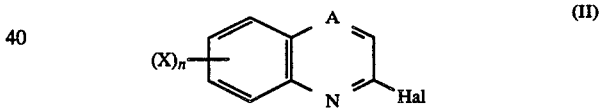

wherein A, X and n are defined above; Hal designates a halogen atom; with 4-hydroxyphenoxy fatty acid derivative having the formula

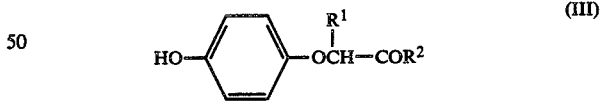

wherein $R^1$ and $R^2$ are defined above, in the presence of an inorganic or organic base such as sodium hydroxide, potassium hydroxide or potassium carbonate, at suitable temperature.

The reaction can be carried out in an inert solvent such as dimethylformamide, dimethylsulfoxide, or acetonitrile.

(B) The compound of the present invention can be produced by a condensation of a compound having the formula (II) with a hydroquinone monobenzyl ether having the formula

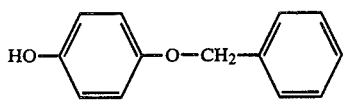

in the presence of an inorganic or organic base to produce a compound having the formula

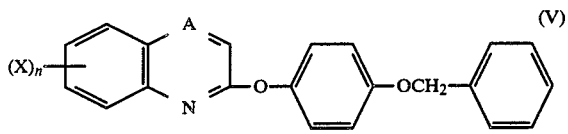

wherein A, X and n are defined above; and then a hydrogenation of the product with a catalyst such as palladium-carbon catalyst to result a debenzylation and to obtain a compound having the formula

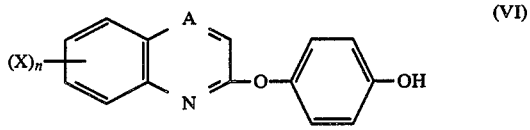

wherein A, X and n are defined above; and then a condensation of the product with an α-halofatty acid derivative having the formula

wherein $R^1$, $R^2$ and Hal are defined above; in the presence of an inorganic or organic base such potassium carbonate in a polar organic solvent such as methyl ethyl ketone, acetonitrile or dimethylformamide.

(C) The product obtained by the process (A) or (B) is converted into the other compounds of the present invention by a hydrolysis, an esterification, an ester interchange, a salt or an amidation.

In the process (A), the reaction is preferably carried out at 50° to 200° C. especially at 80° to 100° C., at a molar ratio of the compound (II):4-hydroxyphenoxy fatty acid derivative (III) of 1:0.2 to 5.0 preferably 1:0.5 to 2.0 especially 1:0.8 to 1.5. The inorganic or organic bases can be any base which is useful for the condensation of the compound (II) and the compound (III). The concentration of the starting materials in the inert solvent can be in a range of 5 to 50 wt.% preferably 10 to 30 wt.%.

In the process (B), the reaction is preferably carried out at 50° to 200° C. especially at 100° to 150° C. at a molar ratio of a compound (II):a hydroquinone monobenzyl ether (IV) of 1:0.2 to 5.0 preferably 1:0.5 to 2.0 especially 1:0.8 to 1.5. The inorganic or organic base can be any base which is useful for the condensation of the compound (II) and the compound (IV). The reaction is preferably carried out in an inert solvent at a concentration of the starting material of 5 to 50 wt.% preferably 10 to 30 wt.%.

The hydrogenation of the resulting intermediate (V) is carried out in the condition for the debenzylation to obtain the compound (VI). The hydrogen pressure is preferably in the range of 1 to 5 atm. preferably 1 to 2 atm.

The reaction of the compound (VI) with the α-halofatty acid derivative (VII) is preferably carried out at 80° to 100° C. at a molar ratio of the compound (VI):-the compound (VII) of 1:0.2 to 5.0 preferably 1:0.5 to 2.0 especially 1:0.8 to 1.5. The inorganic or organic base can be the same ores. The concentration of the starting materials in the inert solvent can be in a range of 5 to 50 wt.% preferably 10 to 30%.

In the process (C), the conditions of the hydrolysis, the esterification, the ester interchange, the neutralization and the amidation can be selected as desired. These conditions can be considered by a person skilled in the art.

Certain examples for the preparations of the present invention will be described.

PREPARATION 1

Methyl 2-[4-(2-quinolyloxy)phenoxy]propionate (Compound No. 2)

In 50 ml of dimethylsulfoxide, 12 g of hydroquinone monobenzyl ether, 8.2 g of 2-chloroquinoline and 8.3 g of potassium carbonate were dissolved and the mixture was heated at 150° to 160° C. for 4 hours to react them. After cooling, the reaction mixture was poured into water and the product was extracted with ether for several times and the ether layer was washed with an aqueous solution of sodium hydroxide and then with water and the ether layer was dehydrated over sodium sulfate. The solvent was distilled off. The resulting crude crystal was washed with diisopropyl ether to obtain 12 g (yield 75%) of 2-(4-benzyloxyphenoxy)-quinoline. All of the intermediate was dissolved in 200 ml of a mixed solvent of tetrahydrofuran and ethanol (5:1) and 1.5 g of palladium-carbon type catalyst was added and 880 ml of hydrogen gas was fed into the mixture to carry out the hydrogenation at the atmospheric pressure. After the hydrogenation, the catalyst was separated by a suction filtration and the solvent was distilled off and the residue was washed with chloroform-n-hexane type solvent to obtain 6.3 g (yield 74%) of white crystal of 2-(4-hydroxyphenoxy)quinoline (m.p. 177° C.).

In 50 ml of methyl ethyl ketone, 2.37 g of the product, 2.1 g of methyl α-bromopropionate and 2.0 g of potassium carbonate were added and the mixture was refluxed for 5 hours to react them. After cooling to the room temperature, the precipitated product was separated by a filtration and the solvent was distilled off to obtain 2.2 g (yield 68%) of the object compound.

PREPARATION 2

2-[4-(2-quinolyloxy)phenoxy]propionic acid N,N-dimethylamide (Compound No. 6)

In 100 ml of methyl ethyl ketone, 2.3 g of the intermediate of Preparation 1 of 2-(4-hydroxyphenoxy)quinoline, 1.8 g of N,N-dimethyl-α-bromopropionic acid amide and 1.4 g of potassium carbonate were added and the mixture was refluxed for 5 hours. After the reaction, the precipitated crystal was separated by a filtration and the solvent was distilled off and the product was dried under a reduced pressure. The resulting crude crystal was recrystallized from a solvent of methanol-water to obtain 3.6 g (yield 88%) of white crystal of the object compound.

PREPARATION 3

Ethyl 2-[4-(2-quinoxalyloxy)phenoxy]propionate
(Compound No. 10)

In 50 ml of acetonitrile, 2.1 g of ethyl 2-(4-hydroxyphenoxy)propionate and 1.66 g of potassium carbonate were added and the mixture was refluxed for 1 hour and then, 1.65 g of 2-chloroquinoxaline was added and the mixture was further refluxed for 30 hours. After cooling, the precipitated inorganic salt was separated by a filtration. Acetone was distilled off from the filtrate under a reduced pressure to obtain 3.5 g of the oily residue. The residue was purified by a silica gel column chromatography (developer solvent: chloroform) to obtain 2.6 g (yield 77%) of the object compound.

PREPARATION 4

2-[4-(2-quinoxalyloxy)phenoxy]propionic acid
(Compound No. 8)

In 10 ml of ethanol, 1.7 g of ester obtained by Preparation 3, and 5 ml of aqueous solution containing 0.3 g of sodium hydroxide were added and the mixture was refluxed for 1 hour. After the reaction, ethanol was distilled off and the remained aqueous solution was acidified with sulfuric acid and the precipitated crystal was separated by a filtration and washed with water and dried to obtain 1.3 g (yield 84%) of white crystal of the object compound.

PREPARATION 5

Methyl 2-[4-(6-chloro-2-quinoxalyloxy)phenoxy]propionate
(Compound No. 22)

In 150 ml of acetonitrile, 2.0 g (0.01 mole) of 2,6-dichloroquinoxaline, 2.0 g (0.01 mole) of methyl 2-(4'-hydroxyphenoxy)propionate and 2.0 g (0.014 mole) of potassium carbonate were added and the mixture was refluxed for 24 hours.

After the reaction, the precipitate was separated by a filtration and the filtrate was concentrated and dried. The residue was dissolved in chloroform and the chloroform solution was washed with 5% aqueous solution of sodium hydroxide and then with water and, dehydrated, condensed and dried. The residual solid product was recrystallized from methanol to obtain 3.1 g (yield 86%) of white crystal of Compound No. 22 having a melting point of 124°–125° C.

PREPARATION 6

2-[4-(6-chloro-2-quinoxalyloxy)phenoxy]propionic acid
(Compound No. 21)

In 20 ml of methanol, 3.6 g (0.01 mole) of the object compound obtained in Preparation 5 and 5 ml of an aqueous solution of 0.5 g (0.013 mole) of sodium hydroxide were added and the mixture was refluxed for 1 hour. After the reaction, the reaction mixture was cooled and filtered. Methanol was distilled off under a reduced pressure from the filtrate. The residual aqueous solution was neutralized with hydrochloric acid and the precipitate was separated by a filtration and washed with water and then with a small amount of methanol and dried to obtain 2.9 g (yield 84%) of white crystal of the object compound having a melting point of 130°–132.5° C.

PREPARATION 7

Methyl D(+)-2-[4-(6-chloro-2-quinoxalyloxy)phenoxy]propionate (Compound No. 74)

In 30 ml of acetonitrile, 1.36 g (5 mmole) of 6-chloro-2-(4'-hydroxy)phenoxyquinoxaline, 1.55 g (6 mmole) of methyl L-(−)-lactate tosylate and 0.83 g (6 mmole) of potassium carbonate were added. The mixture was refluxed for 12 hours. After the reaction, the reaction mixture was cooled. The resulting potassium tosylate and potassium bicarbonate were separated by a suction filtration. The filtrate was concentrated and dried. The residue was dissolved in methylene chloride and a methylene chloride solution was washed twice with water and dried. Methylene chloride was distilled off under a reduced pressure. The resulting crude methyl D(+)-2-[4-(6-chloro-2-quinoxalyloxy)phenoxy]propionate was collected in methylene chloride and was purified by a column chromatography with silica gel to obtain 1.35 (yield 75%) of the purified object compound having $[\alpha]_D^{31} = +32.8°$ C. (chloroform: c=1.20%) and a melting point of 112°–114° C.

EXAMPLE 8

Ethyl 2-[4-(6-fluoro-2-quinoxalyloxy)phenoxy]propionate
(Compound No. 27)

A mixture of 18.3 g. (0.1 mole) of 2-chloro-6-fluoroquinoxaline, 33 g. (0.3 mole) of hydroquinone and 42 g. (0.3 g.) of potassium carbonate was admixed with 500 ml. of acetonitrile and the mixture was refluxed with stirring for 10 hours.

After the reaction, acetonitrile was distilled off under a reduced pressure and the residue was poured on 500 ml. of ice water and acidified with hydrochloric acid. The precipitated crystal was separated by a filtration. The crystal was washed with hot water for several times to remove the unreacted hydroquinone to obtain 19.2 g. of 6-fluoro-2-(4-hydroxyphenoxy)quinoxaline (yield: 75%).

In 100 ml. of methyl ethyl ketone, 2.6 g. (0.01 mole) of the resulting product, 1.8 g. (0.01 mole) of ethyl α-bromopropionate and 1.4 g. (0.01 mole) of potassium carbonate were added. The mixture was refluxed for 10 hours. After the reaction, the precipitated salt was separated by a filtration and a filtrate was distilled off to obtain a viscous oily product. The oily product was purified by a column chromatography with silica gel (chloroform) to obtain 3.2 g. (yield: 89%) of the purified object compound having a melting point of 78° to 79° C.

EXAMPLE 9

Ethyl 2-[4-(6-chloro-2-quinoxalyloxy)phenoxy]propionate
(Compound No. 23)

A mixture of 3.5 g. (0.01 mole) of 2-[4-(6-chloro-2-quinoxalyloxy)phenoxy]propionic acid and 50 ml. of thionyl chloride was refluxed for 10 hours. After the reaction, excess of thionyl chloride was distilled off under a reduced pressure.

The residual oily product was diluted with 30 ml. of anhydrous ether and 1 ml. of triethylamine and 1 ml. of ethyl alcohol were added. The mixture was refluxed for 3 hours. After the reaction, the reaction mixture was poured into water. The organic layer was washed with 5% sodium bicarbonate and then, with water and dehydrated over anhydrous sodium sulfate and ether layer was concentrated to dryness. The resulting oily product was purified by a column chromatography with silica gel (chloroform) to obtain 2.0 g. (yield: 53%) of the purified object compound having a melting point of 84° to 85° C.

EXAMPLE 10

Dimethylamine
2-[4-(6-chloro-2-quinoxalyloxy)phenoxy]propionate
(Compound No. 77)

In 30 ml. of 10% aqueous solution of dimethylamine, 3.4 g. (0.01 mole) of 2-[4-(6-chloro-2-quinoxalyloxy)-phenoxy]propionic acid was added. After a dissolution, excess of dimethylamine and water were removed by evaporating them by a rotary evaporator and the residue was dried in vacuum to obtain 3.5 g. (yield: 91%) of a pale yellow object product having a melting point of 63° to 67° C.

EXAMPLE 11

Diethanolamine
2-[4-(6-chloro-2-quinoxalyloxy)phenoxy]propionate
(Compound No. 73)

In accordance with the process of Example 10 except using diethanolamine instead of diethylamine, the reaction and the treatment were carried out to obtain the object compound.

The compound of the present invention can be used as a herbicidal composition.

In the preparation of the herbicidal compositions, the compound of the present invention can be uniformly mixed with or dissolved in suitable adjuvants such as solid carrier such as clay, talc, bentonite, diatomaceous earth; liquid carrier such as water, alcohols (methanol, ethanol etc.), aromatic hydrocarbons (benzene, toluene, xylene etc.) chlorinated hydrocarbons, ethers, ketones, esters (ethyl acetate etc.), acid amides (dimethylformamide etc.) if desired, with an emulsifier, a dispersing agent, a suspending agent, a wetting agent, a spreader, or a stabilizer to form a solution, an emulsifiable concentrate, a wettable powder, a flowable suspension, a dust or a granule, which is applied if desired, by diluting it with suitable diluent.

It is possible to combine the compound of the present invention with the other herbicide, or an insecticide, a fungicide, a plant growth regulator, a synergism agent.

Certain examples of the herbicidal compositions of the present invention will be illustrated. In the examples, the part means part by weight.

Solution

Active ingredient: 5 to 75 wt. % preferably 10 to 50 wt. % especially 15 to 40 wt. %
Solvent: 95 to 25 wt. % preferably 88 to 30 wt. % especially 82 to 40 wt. %
Surfactant: 1 to 30 wt. % preferably 2 to 20 wt. %

Emulsifiable concentrate

Active ingredient: 2.5 to 50 wt. % preferably 5 to 45 wt. % especially 10 to 40 wt. %
Surfactant: 1 to 30 wt. % preferably 2 to 25 wt. % especially 3 to 20 wt. %
Liquid carrier: 20 to 95 wt. % preferably 30 to 93 wt. % especially 57 to 85 wt. %

Dust

Active ingredient: 0.5 to 10 wt. %
Solid carrier: 99.5 to 90 wt. %

Flowable suspension

Active ingredient: 5–75 wt. % preferably 10–50 wt. %
Water: 94–25 wt. % preferably 90–30 wt. %
Surfactant: 1–30 wt. % preferably 2–20 wt. %

Wettable powder

Active ingredient: 2.5 to 90 wt. % preferably 10 to 80 wt. % especially 20 to 75 wt. %
Surfactant: 0.5 to 20 wt. % preferably 1 to 15 wt. % especially 2 to 10 wt. %
Solid carrier: 5 to 90 wt. % preferably 7.5 to 88 wt. % especially 16 to 56 wt. %

Granule

Active ingredient: 0.5 to 30 wt. %
Solid carrier: 99.5 to 70 wt. %

The emulsifiable concentrate is prepared by dissolving the active ingredient in the liquid carrier with the surfactant. The wettable powder is prepared by admixing the active ingredient with the solid carrier and the surfactant and the mixture is pulverized. The flowable suspension is prepared by suspending and dispersing a finely divided active ingredient into an aqueous solution of a surfactant. The dust, the solution, the granule etc. are prepared by mixing the active ingredient with the adjuvant.

In the following compositions, the following adjuvants are used.

| Sorpol-2680 | |
|---|---|
| POE-hormylnonylphenolether | 50 wt. parts |
| POE-nonylphenolether | 20 wt. parts |
| POE-sorbitan alkyl ester | 10 wt. parts |
| Ca—alkylbenzenesulfonate | 20 wt. parts |
| Sorpol-5039 | |
| POE-alkylarylether sulfate | 50 wt. parts |
| Silica hydrate | 50 wt. parts |
| Carplex | |
| Silica hydrate | 100 wt. parts |
| Zeeklite | |
| Clay | 100 wt. parts |
| Sorpol W-150 | |
| POE-nonylphenolether | 100 wt. parts |

| Composition 1: Wettable powder: | |
|---|---|
| Compound No. 1 | 50 wt. parts |
| Zeeklite A | 46 wt. parts |
| Sorpol 5039 (Toho Chem.) | 2 wt. parts |
| Carplex | 2 wt. parts |

These components were uniformly mixed and pulverized to prepare a wettable powder. The wettable powder was diluted with water at 50 to 1,000 times and the diluted solution was sprayed at a dose of 5 to 1000 g of the active ingredient per 10 ares.

| Composition 2: Emulsifiable concentrate: | |
|---|---|
| Compound No. 4 | 20 wt. parts |
| Xylene | 75 wt. parts |

-continued

| Composition 2: Emulsifiable concentrate: | |
|---|---|
| Sorpol 2680 (Toho Chem.) | 5 wt. parts |

The components were uniformly mixed to prepare an emulsifiable concentrate. The emulsifiable concentrate was diluted with water at 50 to 1,000 times and the diluted solution was sprayed at a dose of 5 to 1000 g of the active ingredient per 10 ares.

| Composition 3: Aqueous solution: | |
|---|---|
| Compound No. 5 | 30 wt. parts |
| Sorpol W-150 (Toho Chem.) | 10 wt. parts |
| Water | 60 wt. parts |

The components were mixed to dissolve them and to prepare an aqueous solution. The aqueous solution was diluted with water at 50 to 1,000 times and the diluted solution was sprayed at a dose of 5 to 1000 g. of the active ingredient per 10 ares.

| Composition 4: Wettable powder: | |
|---|---|
| Compound No. 23 | 80 wt. parts |
| Other hebicide | 20 wt. parts |
| Zeeklite A | 46 wt. parts |
| Sorpol 5039 (Toho Chem.) | 2 wt. parts |
| Carplex | 2 wt. parts |

As the other herbicide, the following known herbicides were respectively used 2-(2,4-dichlorophenoxy)-propionic acid, 2,4-dichlorophenoxyacetic acid, 3-(3-trifluoromethylphenyl)-1,1-dimethylurea, 3-(4-methyl-phenethyloxyphenyl)-1-methyl-1-methoxy urea, 3-(methoxycarbonylamino)-phenyl-N-(3-methylphenyl)carbamate, 3-(ethoxycarbonylamino)-phenyl-N-phenylcarbamate, 3-isopropyl-1H-2,1,3-benzo thiadiazine-(4)-3H-one-2,2-dioxide, 5-amino-4-chloro-2-phenylpyridazine-3-one, 3-cyclohexyl-5,6-trimethyleneuracil, 2-chloro-4-ethylamino-6-isopropylamino-1,3,5-triazine, 2-chloro-4,6-di(ethylamino)-1,3,5-triazine, 2-methylthio-4,6-bis(isopropylamino)-1,3,5-triazine, 4-amino-4,5-dihydro-3-methyl-6-phenyl-1,2,4-triazine-5-one, 4-amino-6-t-butyl-4,5-dihydro-3-methylthio-1,2,4-triazine-5-one, 2-chloro-4-trifluoromethylphenyl-3'-ethoxy-4-nitrophenyl ether or sodium-5-[2-chloro-4-(trifluoromethyl)phenoxy]-2-nitro benzoate.

It is also possible to combine the compound of the present invention with the other herbicidal compounds which are described in "Weed Control Handbook" (Vol. I 6th edition 1977; Vol. II 8th edition 1978) issued by the British Crop Protection Council edited by J. D. Fryer MA & R. J. Makepeace BSc. Blackwell Scientific Publication.

The heterocyclic ether type phenoxy fatty acid derivatives of the present invention impart excellent herbicidal effect to various weeds especially gramineous weeds in a soil treatment or in a foliage treatment, without any phytotoxicity to broad leaf crop plants such as cotton, soybean, radish, cabbage, eggplant, tomato, sugar beet, ground nut, peas, beans, line seed, sun flower, safflower, potato, tabacco, alfalfa, onion etc. Therefore, the heterocyclic ether type phenoxy fatty acid derivatives of the present invention are suitable for selective control of gramineous weeds in a culture of a broad leaf crop plant as herbicide for an agricultural and horticultural field especially up-land.

The heterocyclic ether type phenoxy fatty acid derivatives of the present invention are also effective as herbicides for controlling various weeds in the agricultural and horticultural fields such as up-land, paddy field and orchard as well as non-culturated lands such as playground, vacant land, and rail-way sides, etc.

The herbicidal composition is usually contains 0.5 to 95 wt.% of the compound of the present invention as the active ingredient and the remainder of the adjuvants in the concentrated form. The dose of the compound of the present invention is depending upon a weather condition, a soil condition, a form of a composition, a season of an application and a kind of a crop plant and kinds of weeds and it is usually in a range of 1 to 5000 g preferably 5 to 1000 g of the compound of the invention per 10 ares.

The herbicidal activities of the heterocyclic ether type phenoxy fatty acid derivatives of the present invention will be illustrated in the following tests.

In the following tests, the herbicidal effects of the compounds of the present invention to gramineous weeds including rice are shown together with non-phytotoxicity of the same compounds to broad leaf crop plants as well as broad leaf weeds especially, non-phytotoxicity of the same compounds to broad leaf weeds in post-emergence. These remarkable selectivities have not been found by the other compounds.

TEST 1

Tests for Herbicidal Effect in Soil Treatment

Each plastic box having a length of 15 cm, a width of 22 cm and a depth of 6 cm was filled with a sterilized diluvium soil and seeds of rice (*Oryza sativa*), barnyard grass (*Echinochloa crus-galli*), large crab-grass (*Digitaria adscendens*), lambsquarters (*Chenopodium ficifolium*), common purslane (*Postuloca oleracea*), hairy galinsoga (*Galinsoga ciliata*), yellow cress (*Rorippa atrovirens*) were sown in a depth of about 1.5 cm. Each solution of each herbicidal composition was uniformly sprayed on the surface of the soil to give the specific dose of the active ingredient.

The solution was prepared by diluting, with water, a wettable powder, an emulsifiable concentrate or a solution described in examples of the composition except varying the active ingredient. The solution was sprayed by a small spray. Three weeks after the treatment, the herbicidal effects to rice and various weeds were observed and rated by the following standard. The results are shown in Table 2.

Standard rating

5: Growth control of more than 90% (substantial suppression)
4: Growth control of 70 to 90%
3: Growth control of 40 to 70%
2: Growth control of 20 to 40%
1: Growth control of 5 to 20%
0: Growth control of less than 5% (non-herbicidal effect)

Note

Ri: Rice
Ba.: Barnyard grass
L.C.: Large crab grass
La.: Lambsquarters

C.P.: Common purslane
H.B.: Hairy galinsoga
Y.C.: Yellow cress

TABLE 2-1

| Comp. No. | Dose of Comp. (g/a) | Ri | Ba | L.C. | La. | C.P. | H.G. | Y.C. |
|---|---|---|---|---|---|---|---|---|
| 1 | 100 | 5 | 5 | 5 | 3 | 2 | 2 | 3 |
|   | 50  | 5 | 5 | 5 | 2 | 2 | 2 | 2 |
| 2 | 100 | 5 | 5 | 5 | 3 | 3 | 3 | 4 |
|   | 50  | 5 | 5 | 5 | 1 | 2 | 3 | 3 |
| 3 | 100 | 5 | 5 | 5 | 3 | 4 | 4 | 5 |
|   | 50  | 5 | 5 | 4 | 2 | 3 | 3 | 3 |
| 4 | 100 | 5 | 5 | 5 | 4 | 4 | 4 | 4 |
|   | 50  | 5 | 5 | 5 | 2 | 2 | 3 | 3 |
| 5 | 100 | 5 | 5 | 5 | 2 | 2 | 2 | 2 |
|   | 50  | 5 | 5 | 4 | 2 | 2 | 1 | 1 |
| 6 | 100 | 5 | 5 | 5 | 2 | 0 | 2 | 2 |
|   | 50  | 5 | 5 | 4 | 1 | 0 | 1 | 1 |
| 7 | 100 | 4 | 5 | 4 | 0 | 0 | 2 | 2 |
|   | 50  | 4 | 5 | 4 | 0 | 0 | 1 | 1 |
| 8 | 100 | 5 | 5 | 5 | 1 | 2 | 2 | 2 |
|   | 50  | 5 | 5 | 5 | 1 | 2 | 2 | 2 |
| 9 | 100 | 5 | 5 | 5 | 3 | 1 | 3 | 3 |
|   | 50  | 5 | 5 | 5 | 2 | 0 | 1 | 1 |
| 10 | 100 | 5 | 5 | 5 | 4 | 2 | 3 | 3 |
|    | 50  | 5 | 5 | 5 | 3 | 2 | 2 | 2 |
| 11 | 100 | 5 | 5 | 5 | 0 | 0 | 0 | 0 |
|    | 50  | 5 | 5 | 5 | 0 | 0 | 0 | 0 |
| 12 | 100 | 5 | 5 | 5 | 0 | 0 | 0 | 0 |
|    | 50  | 4 | 5 | 4 | 0 | 0 | 0 | 0 |

TABLE 2-2

| Comp. No. | Dose of Comp. (g/a) | Ri | Ba | L.C. | La. | C.P. | H.G. | Y.C. |
|---|---|---|---|---|---|---|---|---|
| 13 | 100 | 5 | 5 | 5 | 3 | 3 | 3 | 3 |
|    | 50  | 5 | 5 | 5 | 2 | 2 | 2 | 1 |
|    | 25  | 5 | 5 | 5 | 0 | 0 | 0 | 0 |
| 14 | 100 | 5 | 5 | 5 | 3 | 2 | 3 | 3 |
|    | 50  | 5 | 5 | 5 | 2 | 1 | 2 | 2 |
|    | 25  | 5 | 5 | 5 | 0 | 0 | 0 | 0 |
| 15 | 100 | 5 | 5 | 5 | 3 | 3 | 4 | 4 |
|    | 50  | 5 | 5 | 5 | 2 | 2 | 3 | 3 |
|    | 25  | 5 | 5 | 5 | 0 | 0 | 0 | 0 |

TABLE 2-3

| Comp. No. | Dose of Comp. (g/a) | Ri | Ba | L.C. | C.A. | C.P. | H.G. | Y.C. |
|---|---|---|---|---|---|---|---|---|
| 16 | 100 | 5 | 5 | 5 | 2 | 2 | 2 | 2 |
|    | 50  | 5 | 5 | 5 | 1 | 1 | 1 | 0 |
|    | 25  | 5 | 5 | 5 | 0 | 0 | 0 | 0 |
| 17 | 100 | 5 | 5 | 5 | 2 | 2 | 3 | 2 |
|    | 50  | 5 | 5 | 5 | 1 | 1 | 1 | 1 |
|    | 25  | 5 | 5 | 5 | 0 | 0 | 0 | 0 |
| 18 | 100 | 5 | 5 | 5 | 2 | 2 | 2 | 2 |
|    | 50  | 5 | 5 | 5 | 1 | 1 | 1 | 1 |
|    | 25  | 5 | 5 | 5 | 0 | 0 | 0 | 0 |
| 19 | 100 | 5 | 5 | 5 | 2 | 2 | 2 | 2 |
|    | 50  | 5 | 5 | 5 | 1 | 1 | 1 | 1 |
|    | 25  | 5 | 5 | 5 | 0 | 0 | 0 | 0 |
| 20 | 100 | 5 | 5 | 5 | 2 | 2 | 2 | 2 |
|    | 50  | 5 | 5 | 5 | 1 | 1 | 1 | 1 |
|    | 25  | 5 | 5 | 5 | 0 | 0 | 0 | 0 |

TABLE 2-4

| Comp. No. | Dose of Comp. (g/a) | Ri | Ba | L.C. | La. | C.P. | H.G. | Y.C. |
|---|---|---|---|---|---|---|---|---|
| 21 | 100 | 5 | 5 | 5 | 2 | 2 | 2 | 3 |
|    | 50  | 5 | 5 | 5 | 2 | 1 | 1 | 2 |
|    | 25  | 5 | 5 | 5 | 0 | 0 | 0 | 0 |
|    | 12.5| 5 | 5 | 5 | 0 | 0 | 0 | 0 |
| 22 | 100 | 5 | 5 | 5 | 3 | 2 | 2 | 3 |
|    | 50  | 5 | 5 | 5 | 2 | 1 | 1 | 2 |
|    | 25  | 5 | 5 | 5 | 0 | 0 | 0 | 0 |
|    | 12.5| 5 | 5 | 5 | 0 | 0 | 0 | 0 |
| 23 | 100 | 5 | 5 | 5 | 3 | 2 | 2 | 2 |
|    | 50  | 5 | 5 | 5 | 2 | 1 | 1 | 1 |
|    | 25  | 5 | 5 | 5 | 0 | 0 | 0 | 0 |
|    | 12.5| 5 | 5 | 5 | 0 | 0 | 0 | 0 |
| 24 | 100 | 5 | 5 | 5 | 3 | 2 | 2 | 2 |
|    | 50  | 5 | 5 | 5 | 2 | 1 | 1 | 2 |
|    | 25  | 5 | 5 | 5 | 0 | 0 | 0 | 0 |
|    | 12.5| 5 | 5 | 5 | 0 | 0 | 0 | 0 |

TABLE 2-5

| Comp. No. | Dose of Comp. (g/a) | Ri | Ba | L.C. | La. | C.P. | H.G. | Y.C. |
|---|---|---|---|---|---|---|---|---|
| 25 | 100 | 5 | 5 | 5 | 2 | 2 | 2 | 2 |
|    | 50  | 5 | 5 | 5 | 1 | 1 | 1 | 1 |
|    | 25  | 5 | 5 | 5 | 0 | 0 | 0 | 0 |
|    | 12.5| 5 | 5 | 5 | 0 | 0 | 0 | 0 |
| 26 | 100 | 5 | 5 | 5 | 2 | 2 | 2 | 2 |
|    | 50  | 5 | 5 | 5 | 1 | 1 | 1 | 1 |
|    | 25  | 5 | 5 | 5 | 0 | 0 | 0 | 0 |
|    | 12.5| 5 | 5 | 5 | 0 | 0 | 0 | 0 |
| 27 | 100 | 5 | 5 | 5 | 2 | 2 | 2 | 2 |
|    | 50  | 5 | 5 | 5 | 1 | 1 | 1 | 1 |
|    | 25  | 5 | 5 | 5 | 0 | 0 | 0 | 0 |
|    | 12.5| 5 | 5 | 5 | 0 | 0 | 0 | 0 |
| 28 | 100 | 5 | 5 | 5 | 2 | 1 | 1 | 1 |
|    | 50  | 5 | 5 | 5 | 1 | 0 | 0 | 0 |
|    | 25  | 5 | 5 | 5 | 0 | 0 | 0 | 0 |
|    | 12.5| 5 | 5 | 5 | 0 | 0 | 0 | 0 |

TABLE 2-6

| Comp. No. | Dose of Comp. (g/a) | Ri | Ba | L.C. | La. | C.P. | H.G. | Y.C. |
|---|---|---|---|---|---|---|---|---|
| 29 | 100 | 5 | 5 | 5 | 2 | 2 | 2 | 2 |
|    | 50  | 5 | 5 | 5 | 1 | 1 | 1 | 1 |
|    | 25  | 5 | 5 | 5 | 0 | 0 | 0 | 0 |
| 30 | 100 | 5 | 5 | 5 | 2 | 2 | 2 | 2 |
|    | 50  | 5 | 5 | 5 | 1 | 1 | 1 | 1 |
|    | 25  | 5 | 5 | 5 | 0 | 0 | 0 | 0 |
| 31 | 100 | 5 | 5 | 5 | 2 | 2 | 2 | 2 |
|    | 50  | 5 | 5 | 5 | 0 | 1 | 0 | 1 |
|    | 25  | 5 | 5 | 5 | 0 | 0 | 0 | 0 |
| 32 | 100 | 5 | 5 | 5 | 2 | 2 | 2 | 1 |
|    | 50  | 5 | 5 | 5 | 1 | 1 | 1 | 0 |
|    | 25  | 5 | 5 | 5 | 0 | 0 | 0 | 0 |
| 33 | 100 | 5 | 5 | 5 | 2 | 2 | 2 | 2 |
|    | 50  | 5 | 5 | 5 | 1 | 1 | 1 | 1 |
|    | 25  | 5 | 5 | 5 | 0 | 0 | 0 | 0 |
| 34 | 100 | 5 | 5 | 5 | 2 | 2 | 2 | 2 |
|    | 50  | 5 | 5 | 5 | 1 | 1 | 1 | 1 |
|    | 25  | 5 | 5 | 5 | 0 | 0 | 0 | 0 |
| 35 | 100 | 5 | 5 | 5 | 2 | 2 | 2 | 2 |
|    | 50  | 5 | 5 | 5 | 1 | 1 | 1 | 1 |
|    | 25  | 5 | 5 | 5 | 0 | 0 | 0 | 0 |
| 36 | 100 | 5 | 5 | 5 | 2 | 2 | 2 | 2 |
|    | 50  | 5 | 5 | 5 | 1 | 1 | 1 | 1 |
|    | 25  | 5 | 5 | 5 | 0 | 0 | 0 | 0 |
| 37 | 100 | 5 | 5 | 5 | 2 | 2 | 2 | 2 |
|    | 50  | 5 | 5 | 5 | 1 | 1 | 1 | 1 |
|    | 25  | 5 | 5 | 5 | 0 | 0 | 0 | 0 |
| 38 | 100 | 5 | 5 | 5 | 2 | 2 | 2 | 2 |
|    | 50  | 5 | 5 | 5 | 1 | 1 | 1 | 1 |
|    | 25  | 5 | 5 | 5 | 0 | 0 | 0 | 0 |
| 39 | 100 | 5 | 5 | 5 | 1 | 1 | 1 | 1 |
|    | 50  | 5 | 5 | 5 | 0 | 0 | 0 | 0 |
|    | 25  | 5 | 5 | 5 | 0 | 0 | 0 | 0 |
| 40 | 100 | 5 | 5 | 5 | 2 | 2 | 2 | 2 |
|    | 50  | 5 | 5 | 5 | 1 | 1 | 1 | 1 |

TABLE 2-6-continued

| Comp. No. | Dose of Comp. (g/a) | Ri | Ba | L.C. | La. | C.P. | H.G. | Y.C. |
|---|---|---|---|---|---|---|---|---|
| | 25 | 5 | 5 | 5 | 0 | 0 | 0 | 0 |

TABLE 2-7

| Comp. No. | Dose of Comp. (g/a) | Ri | Ba | L.C. | La. | C.P. | H.G. | Y.C. |
|---|---|---|---|---|---|---|---|---|
| 41 | 100 | 5 | 5 | 5 | 2 | 2 | 2 | 1 |
| | 50 | 5 | 5 | 5 | 1 | 1 | 1 | 0 |
| | 25 | 5 | 5 | 5 | 0 | 0 | 0 | 0 |
| 42 | 100 | 5 | 5 | 5 | 2 | 2 | 1 | 1 |
| | 50 | 5 | 5 | 5 | 1 | 1 | 0 | 0 |
| | 25 | 5 | 5 | 5 | 0 | 0 | 0 | 0 |
| 43 | 100 | 5 | 5 | 5 | 1 | 2 | 1 | 1 |
| | 50 | 5 | 5 | 5 | 0 | 1 | 0 | 0 |
| | 25 | 5 | 5 | 5 | 0 | 0 | 0 | 0 |
| 44 | 100 | 5 | 5 | 5 | 1 | 1 | 1 | 1 |
| | 50 | 5 | 5 | 5 | 0 | 1 | 0 | 0 |
| | 25 | 5 | 5 | 5 | 0 | 0 | 0 | 0 |
| 45 | 100 | 5 | 5 | 5 | 1 | 1 | 1 | 1 |
| | 50 | 5 | 5 | 5 | 0 | 0 | 0 | 0 |
| | 25 | 5 | 5 | 5 | 0 | 0 | 0 | 0 |
| 46 | 100 | 5 | 5 | 5 | 2 | 2 | 1 | 1 |
| | 50 | 5 | 5 | 5 | 1 | 1 | 1 | 0 |
| | 25 | 5 | 5 | 5 | 0 | 0 | 0 | 0 |

TABLE 2-8

| Comp. No. | Dose of Comp. (g/a) | Ri | Ba | L.C. | La. | C.P. | H.G. | Y.C. |
|---|---|---|---|---|---|---|---|---|
| 47 | 100 | 5 | 5 | 5 | 2 | 2 | 2 | 2 |
| | 50 | 5 | 5 | 5 | 1 | 1 | 1 | 1 |
| | 25 | 5 | 5 | 5 | 0 | 0 | 0 | 0 |
| | 12.5 | 5 | 5 | 5 | 0 | 0 | 0 | 0 |
| 48 | 100 | 5 | 5 | 5 | 2 | 2 | 2 | 2 |
| | 50 | 5 | 5 | 5 | 1 | 1 | 1 | 1 |
| | 25 | 5 | 5 | 5 | 0 | 0 | 0 | 0 |
| | 12.5 | 5 | 5 | 5 | 0 | 0 | 0 | 0 |
| 49 | 100 | 5 | 5 | 5 | 2 | 2 | 2 | 2 |
| | 50 | 5 | 5 | 5 | 1 | 1 | 1 | 1 |
| | 25 | 5 | 5 | 5 | 0 | 0 | 0 | 0 |
| | 12.5 | 5 | 5 | 5 | 0 | 0 | 0 | 0 |
| 50 | 100 | 5 | 5 | 5 | 2 | 2 | 2 | 2 |
| | 50 | 5 | 5 | 5 | 1 | 1 | 1 | 1 |
| | 25 | 5 | 5 | 5 | 0 | 0 | 0 | 0 |
| | 12.5 | 5 | 5 | 5 | 0 | 0 | 0 | 0 |
| 51 | 100 | 5 | 5 | 5 | 2 | 2 | 2 | 2 |
| | 50 | 5 | 5 | 5 | 1 | 1 | 1 | 1 |
| | 25 | 5 | 5 | 5 | 0 | 0 | 0 | 0 |
| | 12.5 | 5 | 5 | 5 | 0 | 0 | 0 | 0 |
| 52 | 100 | 5 | 5 | 5 | 2 | 2 | 2 | 2 |
| | 50 | 5 | 5 | 5 | 1 | 1 | 1 | 1 |
| | 25 | 5 | 5 | 5 | 0 | 0 | 0 | 0 |
| | 12.5 | 5 | 5 | 5 | 0 | 0 | 0 | 0 |
| 53 | 100 | 5 | 5 | 5 | 2 | 2 | 2 | 2 |
| | 50 | 5 | 5 | 5 | 1 | 1 | 1 | 1 |
| | 25 | 5 | 5 | 5 | 0 | 0 | 0 | 0 |
| | 12.5 | 5 | 5 | 5 | 0 | 0 | 0 | 0 |
| 54 | 100 | 5 | 5 | 5 | 2 | 2 | 2 | 2 |
| | 50 | 5 | 5 | 5 | 1 | 1 | 1 | 1 |
| | 25 | 5 | 5 | 5 | 0 | 0 | 0 | 0 |
| | 12.5 | 5 | 5 | 5 | 0 | 0 | 0 | 0 |
| 55 | 100 | 5 | 5 | 5 | 2 | 2 | 2 | 2 |
| | 50 | 5 | 5 | 5 | 1 | 1 | 1 | 1 |
| | 25 | 5 | 5 | 5 | 0 | 0 | 0 | 0 |
| | 12.5 | 5 | 5 | 5 | 0 | 0 | 0 | 0 |
| 56 | 100 | 5 | 5 | 5 | 2 | 2 | 2 | 2 |
| | 50 | 5 | 5 | 5 | 1 | 1 | 1 | 1 |
| | 25 | 5 | 5 | 5 | 0 | 0 | 0 | 0 |
| | 12.5 | 5 | 5 | 5 | 0 | 0 | 0 | 0 |
| 57 | 100 | 5 | 5 | 5 | 2 | 2 | 2 | 2 |
| | 50 | 5 | 5 | 5 | 1 | 1 | 1 | 1 |
| | 25 | 5 | 5 | 5 | 0 | 0 | 0 | 0 |
| | 12.5 | 5 | 5 | 5 | 0 | 0 | 0 | 0 |
| 58 | 100 | 5 | 5 | 5 | 1 | 1 | 1 | 1 |
| | 50 | 5 | 5 | 5 | 0 | 0 | 0 | 0 |
| | 25 | 5 | 4 | 4 | 0 | 0 | 0 | 0 |
| | 12.5 | 5 | 4 | 4 | 0 | 0 | 0 | 0 |
| 59 | 100 | 5 | 5 | 5 | 2 | 2 | 2 | 2 |
| | 50 | 5 | 5 | 5 | 1 | 1 | 1 | 0 |
| | 25 | 5 | 5 | 5 | 0 | 0 | 0 | 0 |
| | 12.5 | 5 | 5 | 5 | 0 | 0 | 0 | 0 |
| 60 | 100 | 5 | 5 | 5 | 2 | 2 | 2 | 2 |
| | 50 | 5 | 5 | 5 | 1 | 1 | 0 | 0 |
| | 25 | 5 | 5 | 5 | 0 | 0 | 0 | 0 |
| | 12.5 | 5 | 5 | 5 | 0 | 0 | 0 | 0 |
| 61 | 100 | 5 | 5 | 5 | 2 | 2 | 2 | 2 |
| | 50 | 5 | 5 | 5 | 1 | 1 | 1 | 1 |
| | 25 | 5 | 5 | 5 | 0 | 0 | 0 | 0 |
| | 12.5 | 5 | 5 | 5 | 0 | 0 | 0 | 0 |
| 62 | 100 | 5 | 5 | 5 | 2 | 2 | 2 | 2 |
| | 50 | 5 | 5 | 5 | 1 | 1 | 1 | 1 |
| | 25 | 5 | 5 | 5 | 0 | 0 | 0 | 0 |
| | 12.5 | 5 | 5 | 5 | 0 | 0 | 0 | 0 |
| 63 | 100 | 5 | 5 | 5 | 2 | 2 | 2 | 2 |
| | 50 | 5 | 5 | 5 | 1 | 1 | 1 | 1 |
| | 25 | 5 | 5 | 5 | 0 | 0 | 0 | 0 |
| | 12.5 | 5 | 5 | 5 | 0 | 0 | 0 | 0 |
| 64 | 100 | 5 | 5 | 5 | 2 | 2 | 2 | 2 |
| | 50 | 5 | 5 | 5 | 1 | 1 | 1 | 1 |
| | 25 | 5 | 5 | 5 | 0 | 0 | 0 | 0 |
| | 12.5 | 5 | 5 | 5 | 0 | 0 | 0 | 0 |
| 65 | 100 | 5 | 5 | 5 | 2 | 2 | 2 | 2 |
| | 50 | 5 | 5 | 5 | 1 | 1 | 1 | 1 |
| | 25 | 5 | 5 | 5 | 0 | 0 | 0 | 0 |
| | 12.5 | 5 | 5 | 5 | 0 | 0 | 0 | 0 |
| 66 | 100 | 5 | 5 | 5 | 2 | 2 | 2 | 2 |
| | 50 | 5 | 5 | 5 | 1 | 1 | 1 | 1 |
| | 25 | 5 | 5 | 5 | 0 | 0 | 0 | 0 |
| | 12.5 | 5 | 5 | 5 | 0 | 0 | 0 | 0 |

TABLE 2-9

| Comp. No. | Dose of Comp. (g/a) | Ri | Ba | L.C. | La. | C.P. | H.G. | Y.C. |
|---|---|---|---|---|---|---|---|---|
| 67 | 100 | 5 | 5 | 5 | 0 | 0 | 0 | 0 |
| | 50 | 5 | 5 | 5 | 0 | 0 | 0 | 0 |
| | 25 | 4 | 5 | 5 | 0 | 0 | 0 | 0 |
| 68 | 100 | 5 | 5 | 5 | 0 | 0 | 0 | 0 |
| | 50 | 5 | 5 | 5 | 0 | 0 | 0 | 0 |
| | 25 | 4 | 5 | 5 | 0 | 0 | 0 | 0 |
| 69 | 100 | 5 | 5 | 5 | 0 | 0 | 0 | 0 |
| | 50 | 5 | 5 | 5 | 0 | 0 | 0 | 0 |
| | 25 | 4 | 5 | 5 | 0 | 0 | 0 | 0 |
| 70 | 100 | 5 | 5 | 5 | 0 | 0 | 0 | 0 |
| | 50 | 5 | 5 | 5 | 0 | 0 | 0 | 0 |
| | 25 | 4 | 5 | 5 | 0 | 0 | 0 | 0 |
| 71 | 100 | 5 | 5 | 5 | 0 | 0 | 0 | 0 |
| | 50 | 5 | 5 | 5 | 0 | 0 | 0 | 0 |
| | 25 | 4 | 5 | 5 | 0 | 0 | 0 | 0 |

TABLE 2-10

| Comp. No. | Dose of Comp. (g/a) | Ri | Ba | L.C. | La. | C.P. | H.G. | Y.C. |
|---|---|---|---|---|---|---|---|---|
| 78 | 100 | 5 | 5 | 5 | 1 | 1 | 1 | 1 |
| | 50 | 5 | 5 | 5 | 0 | 0 | 0 | 0 |
| | 25 | 5 | 5 | 5 | 0 | 0 | 0 | 0 |
| | 12.5 | 5 | 5 | 5 | 0 | 0 | 0 | 0 |
| 79 | 100 | 5 | 5 | 5 | 1 | 1 | 1 | 1 |
| | 50 | 5 | 5 | 5 | 0 | 0 | 0 | 0 |
| | 25 | 5 | 5 | 5 | 0 | 0 | 0 | 0 |
| | 12.5 | 5 | 5 | 5 | 0 | 0 | 0 | 0 |
| 80 | 100 | 5 | 5 | 5 | 1 | 1 | 1 | 1 |
| | 50 | 5 | 5 | 5 | 0 | 0 | 0 | 0 |
| | 25 | 5 | 5 | 5 | 0 | 0 | 0 | 0 |
| | 12.5 | 5 | 5 | 5 | 0 | 0 | 0 | 0 |
| 81 | 100 | 5 | 5 | 5 | 0 | 0 | 0 | 0 |
| | 50 | 5 | 5 | 5 | 0 | 0 | 0 | 0 |

TABLE 2-10-continued

| Comp. No. | Dose of Comp. (g/a) | Ri | Ba | L.C. | La. | C.P. | H.G. | Y.C. |
|---|---|---|---|---|---|---|---|---|
| | 25 | 5 | 5 | 5 | 0 | 0 | 0 | 0 |
| | 12.5 | 5 | 5 | 5 | 0 | 0 | 0 | 0 |
| 82 | 100 | 5 | 5 | 5 | 0 | 0 | 0 | 0 |
| | 50 | 5 | 5 | 5 | 0 | 0 | 0 | 0 |
| | 25 | 5 | 5 | 5 | 0 | 0 | 0 | 0 |
| | 12.5 | 5 | 5 | 5 | 0 | 0 | 0 | 0 |
| 83 | 100 | 5 | 5 | 5 | 0 | 0 | 0 | 0 |
| | 50 | 5 | 5 | 5 | 0 | 0 | 0 | 0 |
| | 25 | 5 | 5 | 4 | 0 | 0 | 0 | 0 |
| | 12.5 | 4 | 4 | 4 | 0 | 0 | 0 | 0 |

TEST 2

Tests for Herbicidal Effect in Foliage Treatment

Each plastic box having a length of 15 cm, a width of 22 cm, a depth of 6 cm was filled with a sterilized diluvium soil and seeds of rice, large crag-grass, lambsquarts L. var., common purslane, hairy galinsoga, yellow cress and tomato were sown in a form of spots in a depth of about 1.5 cm. When the weeds were grown to 2 to 3 leaf stage, each solution of each herbicidal composition was uniformly sprayed to foliages at each dose of each active ingredient shown in Table 3. The solution was prepared by diluting, with water, a wettable powder, an emulsifiable concentrate or a solution described in examples of the composition except varying the active ingredient and the solution was uniformly sprayed by a small spray on all of foliages of the plants.

Two weeks after the spray treatment, the herbicidal effects to the weeds and tomato were observed and rated by the standard shown in Test 1. The results are shown in Table 3.

TABLE 3-1

| Comp. No. | Dose of Comp. (g/a) | Ri | L.C | La. | C.P. | H.G. | Y.C. | Tomato |
|---|---|---|---|---|---|---|---|---|
| 1 | 100 | 5 | 5 | 2 | 1 | 2 | 3 | 1 |
| | 50 | 5 | 5 | 1 | 0 | 2 | 3 | 1 |
| 2 | 100 | 5 | 5 | 5 | 3 | 2 | 4 | 0 |
| | 50 | 5 | 5 | 5 | 2 | 0 | 3 | 0 |
| 3 | 100 | 5 | 5 | 5 | 3 | 2 | 5 | 1 |
| | 50 | 5 | 4 | 3 | 3 | 2 | 3 | 0 |
| 4 | 100 | 5 | 5 | 3 | 2 | 3 | 4 | 1 |
| | 50 | 5 | 5 | 1 | 1 | 1 | 2 | 0 |
| 5 | 100 | 5 | 5 | 2 | 1 | 2 | 3 | 1 |
| | 50 | 5 | 4 | 2 | 0 | 2 | 2 | 0 |
| 6 | 100 | 3 | 3 | 3 | 0 | 2 | 3 | 0 |
| | 50 | 2 | 2 | 2 | 0 | 1 | 2 | 0 |
| 8 | 100 | 4 | 4 | 2 | 2 | 2 | 2 | 1 |
| | 50 | 4 | 3 | 2 | 2 | 2 | 1 | 0 |
| 9 | 100 | 5 | 4 | 2 | 1 | 2 | 2 | 1 |
| | 50 | 5 | 3 | 1 | 1 | 2 | 2 | 0 |
| 10 | 100 | 5 | 5 | 5 | 2 | 3 | 4 | 0 |
| | 50 | 5 | 4 | 3 | 2 | 2 | 2 | 0 |
| 11 | 100 | 3 | 5 | 0 | 1 | 1 | 0 | 1 |
| | 50 | 3 | 5 | 0 | 1 | 1 | 0 | 0 |

TABLE 3-2

| Comp. No. | Dose of Comp. (g/a) | Ri | L.C. | La. | C.P. | H.G. | Y.C. |
|---|---|---|---|---|---|---|---|
| 13 | 100 | 5 | 5 | 4 | 5 | 3 | 4 |
| | 50 | 5 | 5 | 2 | 3 | 2 | 2 |
| | 25 | 5 | 5 | 0 | 0 | 0 | 0 |
| 14 | 100 | 5 | 5 | 2 | 1 | 2 | 3 |
| | 50 | 5 | 5 | 1 | 1 | 1 | 2 |
| | 25 | 5 | 5 | 1 | 1 | 1 | 2 |
| 15 | 100 | 5 | 5 | 3 | 3 | 2 | 4 |

TABLE 3-2-continued

| Comp. No. | Dose of Comp. (g/a) | Ri | L.C. | La. | C.P. | H.G. | Y.C. |
|---|---|---|---|---|---|---|---|
| | 50 | 5 | 5 | 2 | 2 | 2 | 3 |
| | 25 | 5 | 5 | 1 | 1 | 2 | 2 |

TABLE 3-3

| Comp. No. | Dose of Comp. (g/a) | Ri | L.C. | La. | C.P. | H.G. | Y.C. |
|---|---|---|---|---|---|---|---|
| 16 | 100 | 5 | 5 | 1 | 1 | 2 | 2 |
| | 50 | 5 | 5 | 0 | 0 | 1 | 1 |
| | 25 | 5 | 5 | 0 | 0 | 0 | 0 |
| 17 | 100 | 5 | 5 | 2 | 2 | 2 | 2 |
| | 50 | 5 | 5 | 1 | 1 | 1 | 1 |
| | 25 | 5 | 5 | 0 | 0 | 0 | 0 |
| 18 | 100 | 5 | 5 | 2 | 2 | 2 | 2 |
| | 50 | 5 | 5 | 1 | 1 | 1 | 1 |
| | 25 | 5 | 5 | 0 | 0 | 0 | 0 |
| 19 | 100 | 5 | 5 | 2 | 1 | 2 | 2 |
| | 50 | 5 | 5 | 0 | 0 | 1 | 1 |
| | 25 | 4 | 5 | 0 | 0 | 0 | 0 |
| 20 | 100 | 5 | 5 | 1 | 1 | 2 | 2 |
| | 50 | 5 | 5 | 0 | 0 | 1 | 1 |
| | 25 | 4 | 5 | 0 | 0 | 0 | 0 |

TABLE 3-4

| Comp. No. | Dose of Comp. (g/a) | Ri | Ba | L.C. | La. | C.P. | H.G. | Y.C. |
|---|---|---|---|---|---|---|---|---|
| 21 | 100 | 5 | 5 | 5 | 3 | 3 | 2 | 3 |
| | 50 | 5 | 5 | 5 | 1 | 2 | 1 | 2 |
| | 25 | 5 | 5 | 5 | 0 | 0 | 0 | 0 |
| | 12.5 | 5 | 5 | 5 | 0 | 0 | 0 | 0 |
| 22 | 100 | 5 | 5 | 5 | 2 | 2 | 2 | 3 |
| | 50 | 5 | 5 | 5 | 1 | 1 | 1 | 2 |
| | 25 | 5 | 5 | 5 | 0 | 0 | 0 | 0 |
| | 12.5 | 5 | 5 | 5 | 0 | 0 | 0 | 0 |
| 23 | 100 | 5 | 5 | 5 | 3 | 2 | 2 | 3 |
| | 50 | 5 | 5 | 5 | 2 | 1 | 1 | 1 |
| | 25 | 5 | 5 | 5 | 0 | 0 | 0 | 0 |
| | 12.5 | 5 | 5 | 5 | 0 | 0 | 0 | 0 |
| 24 | 100 | 5 | 5 | 5 | 2 | 3 | 2 | 2 |
| | 50 | 5 | 5 | 5 | 1 | 2 | 1 | 1 |
| | 25 | 5 | 5 | 5 | 0 | 0 | 0 | 0 |
| | 12.5 | 5 | 5 | 5 | 0 | 0 | 0 | 0 |

TABLE 3-5

| Comp. No. | Dose of Comp. (g/a) | Ri | Ba | L.C. | La. | C.P. | H.G. | Y.C. |
|---|---|---|---|---|---|---|---|---|
| 25 | 100 | 5 | 5 | 5 | 2 | 2 | 1 | 2 |
| | 50 | 5 | 5 | 5 | 0 | 1 | 0 | 1 |
| | 25 | 5 | 5 | 5 | 0 | 0 | 0 | 0 |
| | 12.5 | 5 | 5 | 5 | 0 | 0 | 0 | 0 |
| 26 | 100 | 5 | 5 | 5 | 2 | 2 | 2 | 2 |
| | 50 | 5 | 5 | 5 | 0 | 0 | 0 | 1 |
| | 25 | 5 | 5 | 5 | 0 | 0 | 0 | 0 |
| | 12.5 | 5 | 5 | 5 | 0 | 0 | 0 | 0 |
| 27 | 100 | 5 | 5 | 5 | 2 | 2 | 2 | 2 |
| | 50 | 5 | 5 | 5 | 1 | 1 | 1 | 0 |
| | 25 | 5 | 5 | 5 | 0 | 0 | 0 | 0 |
| | 12.5 | 5 | 5 | 5 | 0 | 0 | 0 | 0 |
| 28 | 100 | 5 | 5 | 5 | 2 | 2 | 2 | 2 |
| | 50 | 5 | 5 | 5 | 1 | 1 | 1 | 1 |
| | 25 | 5 | 5 | 5 | 0 | 0 | 0 | 0 |
| | 12.5 | 5 | 5 | 5 | 0 | 0 | 0 | 0 |

TABLE 3-6

| Comp. No. | Dose of Comp. (g/a) | Ri | L.C. | La. | C.P. | H.G. | Y.C. |
|---|---|---|---|---|---|---|---|
| 29 | 100 | 5 | 5 | 2 | 2 | 1 | 2 |
|  | 50 | 5 | 5 | 1 | 1 | 0 | 1 |
|  | 25 | 5 | 5 | 0 | 0 | 0 | 0 |
| 30 | 100 | 5 | 5 | 2 | 2 | 1 | 2 |
|  | 50 | 5 | 5 | 1 | 1 | 0 | 1 |
|  | 25 | 5 | 5 | 0 | 0 | 0 | 0 |
| 31 | 100 | 5 | 5 | 1 | 1 | 1 | 1 |
|  | 50 | 5 | 5 | 0 | 0 | 0 | 0 |
|  | 25 | 4 | 5 | 0 | 0 | 0 | 0 |
| 32 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
| 33 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
| 34 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
| 35 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
| 36 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
| 37 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
| 38 | 100 | 5 | 5 | 1 | 1 | 1 | 2 |
|  | 50 | 5 | 5 | 0 | 0 | 0 | 1 |
|  | 25 | 5 | 5 | 0 | 0 | 0 | 0 |
| 39 | 100 | 5 | 5 | 2 | 1 | 1 | 2 |
|  | 50 | 5 | 5 | 1 | 0 | 0 | 1 |
|  | 25 | 5 | 5 | 0 | 0 | 0 | 0 |
| 40 | 100 | 5 | 5 | 2 | 1 | 1 | 2 |
|  | 50 | 5 | 5 | 1 | 0 | 0 | 1 |
|  | 25 | 5 | 5 | 0 | 0 | 0 | 0 |

TABLE 3-7

| Comp. No. | Dose of Comp. (g/a) | Ri | L.C. | La. | C.P. | H.G. | Y.C. |
|---|---|---|---|---|---|---|---|
| 41 | 100 | 5 | 5 | 2 | 1 | 2 | 1 |
|  | 50 | 5 | 5 | 1 | 0 | 1 | 0 |
|  | 25 | 5 | 5 | 0 | 0 | 0 | 0 |
| 42 | 100 | 5 | 5 | 2 | 1 | 2 | 1 |
|  | 50 | 5 | 5 | 0 | 0 | 1 | 0 |
|  | 25 | 5 | 5 | 0 | 0 | 0 | 0 |
| 43 | 100 | 5 | 5 | 2 | 2 | 2 | 1 |
|  | 50 | 5 | 5 | 1 | 0 | 1 | 0 |
|  | 25 | 5 | 5 | 0 | 0 | 0 | 0 |
| 44 | 100 | 5 | 5 | 1 | 1 | 1 | 1 |
|  | 50 | 5 | 5 | 0 | 0 | 0 | 0 |
|  | 25 | 5 | 5 | 0 | 0 | 0 | 0 |
| 45 | 100 | 5 | 5 | 1 | 1 | 1 | 1 |
|  | 50 | 5 | 5 | 0 | 0 | 0 | 0 |
|  | 25 | 4 | 4 | 0 | 0 | 0 | 0 |
| 46 | 100 | 5 | 5 | 2 | 2 | 2 | 1 |
|  | 50 | 5 | 5 | 1 | 0 | 1 | 0 |
|  | 25 | 5 | 5 | 0 | 0 | 0 | 0 |

TABLE 3-8

| Comp. No. | Dose of Comp. (g/a) | Ri | L.C. | La. | C.P. | H.G. | Y.C. |
|---|---|---|---|---|---|---|---|
| 47 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
|  | 12.5 | 5 | 5 | 0 | 0 | 0 | 0 |
| 48 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
|  | 12.5 | 5 | 5 | 0 | 0 | 0 | 0 |
| 49 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
|  | 12.5 | 5 | 5 | 0 | 0 | 0 | 0 |
| 50 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
|  | 12.5 | 5 | 5 | 0 | 0 | 0 | 0 |
| 51 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
|  | 12.5 | 5 | 5 | 0 | 0 | 0 | 0 |
| 52 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
|  | 12.5 | 5 | 5 | 0 | 0 | 0 | 0 |
| 53 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
|  | 12.5 | 5 | 5 | 0 | 0 | 0 | 0 |
| 54 | 100 | 5 | 5 | 1 | 1 | 1 | 1 |
|  | 50 | 5 | 5 | 1 | 0 | 1 | 1 |
|  | 25 | 5 | 5 | 0 | 0 | 0 | 0 |
|  | 12.5 | 5 | 5 | 0 | 0 | 0 | 0 |
| 55 | 100 | 5 | 5 | 1 | 1 | 1 | 1 |
|  | 50 | 5 | 5 | 1 | 0 | 0 | 0 |
|  | 25 | 5 | 5 | 0 | 0 | 0 | 0 |
|  | 12.5 | 5 | 5 | 0 | 0 | 0 | 0 |
| 56 | 100 | 5 | 5 | 1 | 1 | 1 | 1 |
|  | 50 | 5 | 5 | 0 | 0 | 0 | 0 |
|  | 25 | 5 | 5 | 0 | 0 | 0 | 0 |
|  | 12.5 | 5 | 5 | 0 | 0 | 0 | 0 |
| 57 | 100 | 5 | 5 | 1 | 1 | 1 | 1 |
|  | 50 | 5 | 5 | 0 | 0 | 0 | 0 |
|  | 25 | 5 | 5 | 0 | 0 | 0 | 0 |
|  | 12.5 | 5 | 5 | 0 | 0 | 0 | 0 |
| 58 | 100 | 5 | 5 | 0 | 0 | 0 | 0 |
|  | 50 | 5 | 5 | 0 | 0 | 0 | 0 |
|  | 25 | 5 | 5 | 0 | 0 | 0 | 0 |
|  | 12.5 | 5 | 5 | 0 | 0 | 0 | 0 |
| 59 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
|  | 12.5 | 5 | 5 | 0 | 0 | 0 | 0 |
| 60 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
|  | 12.5 | 5 | 5 | 0 | 0 | 0 | 0 |
| 61 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
|  | 12.5 | 5 | 5 | 0 | 0 | 0 | 0 |
| 62 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
|  | 12.5 | 5 | 5 | 0 | 0 | 0 | 0 |
| 63 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
|  | 12.5 | 5 | 5 | 0 | 0 | 0 | 0 |
| 64 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
|  | 12.5 | 5 | 5 | 0 | 0 | 0 | 0 |
| 65 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
|  | 12.5 | 5 | 5 | 0 | 0 | 0 | 0 |
| 66 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
|  | 12.5 | 5 | 5 | 0 | 0 | 0 | 0 |

TABLE 3-9

| Comp. No. | Dose of Comp. (g/a) | Ri | L.C. | La. | C.P. | H.G. | Y.C. |
|---|---|---|---|---|---|---|---|
| 67 | 100 | 5 | 5 | 0 | 0 | 1 | 0 |

TABLE 3-9-continued

| Comp. No. | Dose of Comp. (g/a) | Ri | L.C. | La. | C.P. | H.G. | Y.C. |
|---|---|---|---|---|---|---|---|
|  | 50 | 5 | 5 | 0 | 0 | 0 | 0 |
|  | 25 | 3 | 5 | 0 | 0 | 0 | 0 |
| 68 | 100 | 5 | 5 | 0 | 1 | 1 | 0 |
|  | 50 | 4 | 5 | 0 | 0 | 0 | 0 |
|  | 25 | 4 | 5 | 0 | 0 | 0 | 0 |
| 69 | 100 | 5 | 5 | 0 | 0 | 0 | 0 |
|  | 50 | 4 | 5 | 0 | 0 | 0 | 0 |
|  | 25 | 3 | 5 | 0 | 0 | 0 | 0 |
| 70 | 100 | 5 | 5 | 0 | 0 | 0 | 0 |
|  | 50 | 4 | 5 | 0 | 0 | 0 | 0 |
|  | 25 | 3 | 5 | 0 | 0 | 0 | 0 |
| 71 | 100 | 4 | 5 | 0 | 0 | 0 | 0 |
|  | 50 | 3 | 4 | 0 | 0 | 0 | 0 |
|  | 25 | 3 | 4 | 0 | 0 | 0 | 0 |

TABLE 3-10

| Comp. No. | Dose of Comp. (g/a) | Ri | L.C. | La. | C.P. | H.G. | Y.C. |
|---|---|---|---|---|---|---|---|
| 72 | 50 | 5 | 5 | 0 | 0 | 0 | 0 |
|  | 25 | 5 | 5 | 0 | 0 | 0 | 0 |
| 73 | 50 | 5 | 5 | 0 | 0 | 0 | 0 |
|  | 25 | 5 | 5 | 0 | 0 | 0 | 0 |
| 74 | 50 | 5 | 5 | 0 | 0 | 0 | 0 |
|  | 25 | 5 | 0 | 0 | 0 | 0 | 0 |
| 75 | 50 | 5 | 5 | 0 | 0 | 0 | 0 |
|  | 25 | 5 | 5 | 0 | 0 | 0 | 0 |
| 76 | 50 | 5 | 5 | 0 | 0 | 0 | 0 |
|  | 25 | 5 | 5 | 0 | 0 | 0 | 0 |
| 77 | 50 | 5 | 5 | 0 | 0 | 0 | 0 |
|  | 25 | 5 | 5 | 0 | 0 | 0 | 0 |

TABLE 3-11

| Comp. No. | Dose of Comp. (g/a) | Ri | L.C. | La. | C.P. | H.G. | Y.C. |
|---|---|---|---|---|---|---|---|
| 78 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
|  | 12.5 | 5 | 5 | 0 | 0 | 0 | 0 |
| 79 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
|  | 12.5 | 5 | 5 | 0 | 0 | 0 | 0 |
| 80 | 100 | 5 | 5 | 2 | 2 | 2 | 2 |
|  | 50 | 5 | 5 | 1 | 1 | 1 | 1 |
|  | 25 | 5 | 5 | 0 | 0 | 0 | 0 |
|  | 12.5 | 5 | 5 | 0 | 0 | 0 | 0 |
| 81 | 100 | 5 | 5 | 1 | 1 | 1 | 1 |
|  | 50 | 5 | 5 | 0 | 0 | 0 | 0 |
|  | 25 | 5 | 5 | 0 | 0 | 0 | 0 |
|  | 12.5 | 5 | 5 | 0 | 0 | 0 | 0 |
| 82 | 100 | 5 | 5 | 1 | 1 | 1 | 1 |
|  | 50 | 5 | 5 | 0 | 0 | 0 | 0 |
|  | 25 | 5 | 5 | 0 | 0 | 0 | 0 |
|  | 12.5 | 5 | 5 | 0 | 0 | 0 | 0 |
| 83 | 100 | 5 | 5 | 0 | 0 | 0 | 0 |
|  | 50 | 5 | 5 | 0 | 0 | 0 | 0 |
|  | 25 | 5 | 5 | 0 | 0 | 0 | 0 |
|  | 12.5 | 5 | 5 | 0 | 0 | 0 | 0 |

TEST 3

Tests for Phytotoxicity to Crop Plants (Foliage Treatment)

Each plastic box having a length of 15 cm, a width of 22 cm, and a depth of 6 cm was filled with a sterilized diluvium soil and seeds of cotton, soybean, radish, cabbage and eggplant were sown in a form of spots in a depth of about 1.5 cm. When the plants were grown to leaf-emergence stage, each solution of each herbicidal composition was uniformly sprayed to foliages at each dose of each active ingredient shown in Table 4. The solution was prepared by diluting, with water, a wettable powder, an emulsifiable concentrate or a solution described in examples of the composition except varying the active ingredient and the solution was uniformly sprayed by a small spray on all of foliages of the plants.

Two weeks after the spray treatment, the phytotoxicities to the plants were observed and rated by the following standard. The results are shown in Table 4.

Standard rating

5: Complete death of plant
4: Serious phytotoxicity to plant
3: Fair phytotoxicity to plant
2: Slight phytotoxicity to plant
1: Only slight phytotoxicity to plant
0: Non phytotoxicity Note Cot.: Cotton
Soy.: Soybean
Rad.: Radish
Cab.: Cabbage
Egg.: Eggplant

TABLE 4-1

| Compound No. | Dose of Compound (g/a) | Cot. | Soy. | Rad. | Cab. | Egg. |
|---|---|---|---|---|---|---|
| 2 | 50 | 1 | 0 | 1 | 0 | 0 |
|  | 25 | 0 | 0 | 0 | 0 | 0 |
| 4 | 50 | 1 | 1 | 1 | 1 | 1 |
|  | 25 | 1 | 0 | 0 | 1 | 0 |
| 10 | 50 | 0 | 0 | 1 | 0 | 0 |
|  | 25 | 0 | 0 | 0 | 0 | 0 |

TABLE 4-2

| Compound No. | Dose of Compound (g/a) | Cot. | Soy. | Rad. | Cab. | Egg. |
|---|---|---|---|---|---|---|
| 13 | 50 | 1 | 0 | 1 | 0 | 0 |
|  | 25 | 0 | 0 | 0 | 0 | 0 |
| 14 | 50 | 1 | 1 | 0 | 0 | 0 |
|  | 25 | 0 | 0 | 0 | 0 | 0 |
| 15 | 50 | 1 | 1 | 0 | 0 | 0 |
|  | 25 | 0 | 0 | 0 | 0 | 0 |

TABLE 4-3

| Compound No. | Dose of Compound (g/a) | Cot. | Soy. | Rad. | Cab. | Egg. |
|---|---|---|---|---|---|---|
| 16 | 50 | 0 | 1 | 0 | 0 | 0 |
|  | 25 | 0 | 0 | 0 | 0 | 0 |
| 17 | 50 | 0 | 1 | 0 | 0 | 0 |
|  | 25 | 0 | 0 | 0 | 0 | 0 |
| 18 | 50 | 0 | 1 | 0 | 0 | 0 |
|  | 25 | 0 | 0 | 0 | 0 | 0 |
| 19 | 50 | 0 | 0 | 0 | 0 | 0 |
|  | 25 | 0 | 0 | 0 | 0 | 0 |
| 20 | 50 | 0 | 0 | 0 | 0 | 0 |
|  | 25 | 0 | 0 | 0 | 0 | 0 |

TABLE 4-4

| Compound No. | Dose of Compound (g/a) | Cot. | Soy. | Rad. | Cab. | Egg. |
|---|---|---|---|---|---|---|
| 21 | 50 | 0 | 1 | 1 | 1 | 0 |
|  | 25 | 0 | 0 | 0 | 0 | 0 |

TABLE 4-10-continued

| Compound No. | Dose of Compound (g/a) | Cot. | Soy. | Rad. | Cab. | Egg. |
|---|---|---|---|---|---|---|
| | 25 | 0 | 0 | 0 | 0 | 0 |
| 83 | 100 | 0 | 0 | 0 | 0 | 0 |
| | 50 | 0 | 0 | 0 | 0 | 0 |
| | 25 | 0 | 0 | 0 | 0 | 0 |

What is claimed is:

1. Heterocyclic ether type phenoxy fatty acid derivatives having the formula

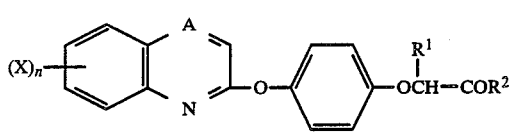 (I)

wherein A represents —N—; X represents halogen; n is 0, 1 or 2; $R^1$ represents hydrogen or lower alkyl; $R^2$ represents —OH; —O—alkyl, —OM, wherein M is lower alkyl ammonium, ethanolammonium, lower alkyl ethanolammonium, alkali metal or alkaline earth metal;

—O—lower alkenyl; —O—benzyl; —O—lower alkylalkoxy; —O—phenyl; —O—cyclohexyl; —O—halogenoalkyl; —O—lower alkynyl or —O—cyanoalkyl; and $R^3$ and $R^4$ respectively represent hydrogen or lower alkyl.

2. Heterocyclic ether type phenoxy fatty acid derivatives according to claim 1 which have the formula I wherein $R^2$ is —OH; —O—alkyl; —OM, wherein M is lower alkyl ammonium, ethanolammonium, lower alkyl ethanolammonium, alkali metal or alkaline earth; or

3. Heterocyclic ether type phenoxy fatty acid derivatives having the formula

wherein X represents halogen and $R^5$ represents hydrogen, lower alkyl, lower alkylammonium, ethanolammonium, lower alkyl ethanolammonium, alkali metal or alkaline earth metal.

4. A herbicidal composition consisting essentially of an agriculturally acceptable adjuvant and an active ingredient of heterocyclic ether type phenoxy fatty acid derivative having the formula

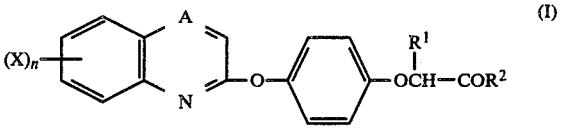 (I)

wherein A represents —N—; X represents halogen; n is 0, 1 or 2; $R^1$ represents hydrogen or lower alkyl; $R^2$ represents —OH; —O—alkyl; —OM; wherein M is lower alkyl ammonium, lower alkyl ethanolammonium, alkali metal or alkaline earth;

—O—lower alkenyl; —O—lower alkylalkoxy; —O—phenyl; —O—cyclohexyl; —O—halogenoalkyl; —O—lower alkynyl or —O—cyanoalkyl; and $R^3$ and $R^4$ respectively represent hydrogen or lower alkyl.

5. A herbicidal composition according to claim 4 wherein $R^2$ is —OH; —O—alkyl; —OM, wherein M is lower alkyl ammonium, ethanolammonium, lower alkyl ethanolammonium, alkali metal or alkaline earth or

6. A herbicidal composition according to claim 4 which consists essentially of 0.5 to 95 wt. % of the active ingredient and 99.5 to 5 wt. % of an agriculturally acceptable adjuvant.

7. A herbicidal composition according to claim 4 which is in a form of a solution, an emulsifiable concentrate or a wettable powder.

8. A herbicidal composition according to claim 5 which consists essentially of 0.5 to 95 wt. % of the active ingredient and and 99.5 to 5 wt. % of an agriculturally acceptable adjuvant.

9. A method for controlling the growth of undesired vegitation which comprises applying to the locus to be protected an effective amount of a compound of claim 1.

10. A herbicidal composition according to claim 5 which is in a form of a solution, an emulsifiable concentrate or wettable powder.

11. A herbicidal composition according to claim 5 which is in a form of a flowable suspension.

12. A herbicidal composition according to claim 5 which is in a form of a granule.

13. A herbicidal composition according to claim 5 which is in a form of a dust.

14. Heterocyclic ether type phenoxy fatty acid derivatives according to claim 1 which are the D-enantiomers.

15. Heterocyclic ether type phenoxy fatty acid derivatives according to claim 3 which are the D-enantiomers.

16. A herbicidal composition according to claim 5 wherein the heterocyclic ether type phenoxy fatty acid derivative is the D-enantiomer.

17. A herbicidal composition according to claim 4 wherein the heterocyclic ether type phenoxy fatty acid derivative is the D-enantiomer.

* * * * *

TABLE 4-4-continued

| Compound No. | Dose of Compound (g/a) | Cot. | Soy. | Rad. | Cab. | Egg. |
|---|---|---|---|---|---|---|
| 22 | 50 | 0 | 1 | 1 | 1 | 0 |
|    | 25 | 0 | 0 | 0 | 0 | 0 |
| 23 | 50 | 0 | 1 | 1 | 1 | 0 |
|    | 25 | 0 | 0 | 0 | 0 | 0 |
| 24 | 50 | 0 | 1 | 1 | 1 | 0 |
|    | 25 | 0 | 0 | 0 | 0 | 0 |

TABLE 4-5

| Compound No. | Dose of Compound (g/a) | Cot. | Soy. | Rad. | Cab. | Egg. |
|---|---|---|---|---|---|---|
| 25 | 50 | 0 | 0 | 0 | 0 | 0 |
|    | 25 | 0 | 0 | 0 | 0 | 0 |
| 26 | 50 | 0 | 0 | 0 | 0 | 0 |
|    | 25 | 0 | 0 | 0 | 0 | 0 |
| 27 | 50 | 0 | 0 | 0 | 0 | 0 |
|    | 25 | 0 | 0 | 0 | 0 | 0 |
| 28 | 50 | 0 | 0 | 0 | 0 | 0 |
|    | 25 | 0 | 0 | 0 | 0 | 0 |

TABLE 4-6

| Compound No. | Dose of Compound (g/a) | Cot. | Soy. | Rad. | Cab. | Egg. |
|---|---|---|---|---|---|---|
| 29 | 50 | 0 | 1 | 1 | 1 | 0 |
|    | 25 | 0 | 0 | 0 | 0 | 0 |
| 30 | 50 | 0 | 1 | 1 | 1 | 1 |
|    | 25 | 0 | 0 | 0 | 0 | 0 |
| 31 | 50 | 0 | 0 | 0 | 0 | 0 |
|    | 25 | 0 | 0 | 0 | 0 | 0 |
| 32 | 50 | 0 | 1 | 1 | 1 | 1 |
|    | 25 | 0 | 0 | 0 | 0 | 0 |
| 33 | 50 | 0 | 1 | 1 | 1 | 1 |
|    | 25 | 0 | 0 | 0 | 0 | 0 |
| 34 | 50 | 0 | 1 | 1 | 1 | 1 |
|    | 25 | 0 | 0 | 0 | 0 | 0 |
| 35 | 50 | 0 | 1 | 1 | 1 | 1 |
|    | 25 | 0 | 0 | 0 | 0 | 0 |
| 36 | 50 | 0 | 1 | 1 | 1 | 1 |
|    | 25 | 0 | 0 | 0 | 0 | 0 |
| 37 | 50 | 0 | 1 | 1 | 1 | 1 |
|    | 25 | 0 | 0 | 0 | 0 | 0 |
| 38 | 50 | 0 | 0 | 1 | 1 | 0 |
|    | 25 | 0 | 0 | 0 | 0 | 0 |
| 39 | 50 | 0 | 1 | 0 | 0 | 0 |
|    | 25 | 0 | 0 | 0 | 0 | 0 |
| 40 | 50 | 0 | 1 | 1 | 0 | 0 |
|    | 25 | 0 | 0 | 0 | 0 | 0 |

TABLE 4-7

| Compound No. | Dose of Compound (g/a) | Cot. | Soy. | Rad. | Cab. | Egg. |
|---|---|---|---|---|---|---|
| 41 | 50 | 0 | 0 | 0 | 0 | 0 |
|    | 25 | 0 | 0 | 0 | 0 | 0 |
| 42 | 50 | 0 | 0 | 0 | 0 | 0 |
|    | 25 | 0 | 0 | 0 | 0 | 0 |
| 43 | 50 | 0 | 0 | 0 | 0 | 0 |
|    | 25 | 0 | 0 | 0 | 0 | 0 |
| 44 | 50 | 0 | 0 | 0 | 0 | 0 |
|    | 25 | 0 | 0 | 0 | 0 | 0 |
| 45 | 50 | 0 | 0 | 0 | 0 | 0 |
|    | 25 | 0 | 0 | 0 | 0 | 0 |
| 46 | 50 | 0 | 0 | 0 | 0 | 0 |
|    | 25 | 0 | 0 | 0 | 0 | 0 |

TABLE 4-8

| Compound No. | Dose of Compound (g/a) | Cot. | Soy. | Rad. | Cab. | Egg. |
|---|---|---|---|---|---|---|
| 47 | 100 | 0 | 1 | 1 | 0 | 0 |
|    | 50  | 0 | 0 | 0 | 0 | 0 |
| 48 | 100 | 0 | 1 | 1 | 0 | 0 |
|    | 50  | 0 | 0 | 0 | 0 | 0 |
| 49 | 100 | 0 | 0 | 0 | 0 | 0 |
|    | 50  | 0 | 0 | 0 | 0 | 0 |
| 50 | 100 | 0 | 0 | 0 | 0 | 0 |
|    | 50  | 0 | 0 | 0 | 0 | 0 |
| 51 | 100 | 0 | 0 | 0 | 0 | 0 |
|    | 50  | 0 | 0 | 0 | 0 | 0 |
| 52 | 100 | 0 | 0 | 0 | 0 | 0 |
|    | 50  | 0 | 0 | 0 | 0 | 0 |
| 53 | 100 | 0 | 0 | 0 | 0 | 0 |
|    | 50  | 0 | 0 | 0 | 0 | 0 |
| 54 | 100 | 0 | 0 | 0 | 0 | 0 |
|    | 50  | 0 | 0 | 0 | 0 | 0 |
| 55 | 100 | 0 | 0 | 0 | 0 | 0 |
|    | 50  | 0 | 0 | 0 | 0 | 0 |
| 56 | 100 | 0 | 0 | 0 | 0 | 0 |
|    | 50  | 0 | 0 | 0 | 0 | 0 |
| 57 | 100 | 0 | 1 | 0 | 0 | 0 |
|    | 50  | 0 | 0 | 0 | 0 | 0 |
| 58 | 100 | 0 | 0 | 0 | 0 | 0 |
|    | 50  | 0 | 0 | 0 | 0 | 0 |
| 59 | 100 | 0 | 0 | 0 | 0 | 0 |
|    | 50  | 0 | 0 | 0 | 0 | 0 |
| 60 | 100 | 0 | 0 | 0 | 0 | 0 |
|    | 50  | 0 | 0 | 0 | 0 | 0 |
| 61 | 100 | 0 | 0 | 0 | 0 | 0 |
|    | 50  | 0 | 0 | 0 | 0 | 0 |
| 62 | 100 | 0 | 0 | 0 | 0 | 0 |
|    | 50  | 0 | 0 | 0 | 0 | 0 |
| 63 | 100 | 0 | 0 | 0 | 0 | 0 |
|    | 50  | 0 | 0 | 0 | 0 | 0 |
| 64 | 100 | 0 | 0 | 0 | 0 | 0 |
|    | 50  | 0 | 0 | 0 | 0 | 0 |
| 65 | 100 | 0 | 0 | 0 | 0 | 0 |
|    | 50  | 0 | 0 | 0 | 0 | 0 |
| 66 | 100 | 0 | 0 | 0 | 0 | 0 |
|    | 50  | 0 | 0 | 0 | 0 | 0 |

TABLE 4-9

| Compound No. | Dose of Compound (g/a) | Cot. | Soy. | Rad. | Cab. | Egg. |
|---|---|---|---|---|---|---|
| 67 | 50 | 0 | 0 | 0 | 0 | 0 |
|    | 25 | 0 | 0 | 0 | 0 | 0 |
| 68 | 50 | 0 | 0 | 0 | 0 | 0 |
|    | 25 | 0 | 0 | 0 | 0 | 0 |
| 69 | 50 | 0 | 0 | 0 | 0 | 0 |
|    | 25 | 0 | 0 | 0 | 0 | 0 |
| 70 | 50 | 0 | 0 | 0 | 0 | 0 |
|    | 25 | 0 | 0 | 0 | 0 | 0 |
| 71 | 50 | 0 | 0 | 0 | 0 | 0 |
|    | 25 | 0 | 0 | 0 | 0 | 0 |

TABLE 4-10

| Compound No. | Dose of Compound (g/a) | Cot. | Soy. | Rad. | Cab. | Egg. |
|---|---|---|---|---|---|---|
| 78 | 100 | 1 | 0 | 1 | 0 | 0 |
|    | 50  | 0 | 0 | 0 | 0 | 0 |
|    | 25  | 0 | 0 | 0 | 0 | 0 |
| 79 | 100 | 1 | 0 | 1 | 0 | 0 |
|    | 50  | 0 | 0 | 0 | 0 | 0 |
|    | 25  | 0 | 0 | 0 | 0 | 0 |
| 80 | 100 | 1 | 1 | 1 | 0 | 0 |
|    | 50  | 0 | 0 | 0 | 0 | 0 |
|    | 25  | 0 | 0 | 0 | 0 | 0 |
| 81 | 100 | 1 | 1 | 0 | 0 | 0 |
|    | 50  | 0 | 0 | 0 | 0 | 0 |
|    | 25  | 0 | 0 | 0 | 0 | 0 |
| 82 | 100 | 0 | 0 | 0 | 0 | 0 |
|    | 50  | 0 | 0 | 0 | 0 | 0 |